US009328077B2

(12) United States Patent
Salituro et al.

(10) Patent No.: US 9,328,077 B2
(45) Date of Patent: May 3, 2016

(54) BICYCLIC PKM2 ACTIVATORS

(75) Inventors: Francesco G. Salituro, Marlborough, MA (US); Jeffrey O. Saunders, Lincoln, MA (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 0 days.

(21) Appl. No.: 13/996,286

(22) PCT Filed: Dec. 21, 2011

(86) PCT No.: PCT/US2011/066595
§ 371 (c)(1),
(2), (4) Date: Sep. 30, 2013

(87) PCT Pub. No.: WO2012/088314
PCT Pub. Date: Jun. 28, 2012

(65) Prior Publication Data
US 2014/0011804 A1 Jan. 9, 2014

Related U.S. Application Data

(60) Provisional application No. 61/425,557, filed on Dec. 21, 2010, provisional application No. 61/425,499, filed on Dec. 21, 2010, provisional application No. 61/425,513, filed on Dec. 21, 2010, provisional application No. 61/425,528, filed on Dec. 21, 2010.

(51) Int. Cl.
*C07D 265/36* (2006.01)
*C07D 265/18* (2006.01)
*C07D 413/12* (2006.01)

(52) U.S. Cl.
CPC ............ *C07D 265/36* (2013.01); *C07D 265/18* (2013.01); *C07D 413/12* (2013.01)

(58) Field of Classification Search
CPC ... C07D 265/36; C07D 265/18; C07D 413/12
USPC ....................... 544/105; 514/230.5
See application file for complete search history.

(56) References Cited

U.S. PATENT DOCUMENTS

| | | |
|---|---|---|
| 3,046,122 A | 7/1962 | Oskar Siis et al. |
| 3,097,210 A | 7/1963 | Bicking |
| 3,998,828 A | 12/1976 | Wiedermann |
| 4,235,871 A | 11/1980 | Papahadjopoulos et al. |
| 4,315,940 A | 2/1982 | Hitzel et al. |
| 4,474,599 A | 10/1984 | Rogers et al. |
| 4,501,728 A | 2/1985 | Geho et al. |
| 4,591,548 A * | 5/1986 | Delprato ............... 430/389 |
| 4,593,102 A | 6/1986 | Shanklin, Jr. |
| 4,775,762 A | 10/1988 | Knox et al. |
| 4,837,028 A | 6/1989 | Allen |
| 4,849,424 A | 7/1989 | Ikeda et al. |
| 4,881,965 A | 11/1989 | Yamamoto et al. |
| 4,889,553 A | 12/1989 | Rowson et al. |
| 4,959,094 A | 9/1990 | Wegner et al. |
| 5,019,369 A | 5/1991 | Presant et al. |
| 5,122,530 A | 6/1992 | Tomioka et al. |
| 5,180,732 A | 1/1993 | Tomioka et al. |
| 5,220,028 A | 6/1993 | Iwasawa et al. |
| 5,252,590 A | 10/1993 | Tomioka et al. |
| 5,556,866 A | 9/1996 | Aga et al. |
| 5,834,485 A | 11/1998 | Dyke et al. |
| 5,843,485 A | 12/1998 | Fernandez et al. |
| 5,962,490 A | 10/1999 | Chan et al. |
| 5,965,559 A | 10/1999 | Faull et al. |
| 5,965,569 A | 10/1999 | Camps Garcia et al. |
| 6,020,357 A | 2/2000 | Pinto et al. |
| 6,106,849 A | 8/2000 | Malkan et al. |
| 6,150,356 A | 11/2000 | Lloyd et al. |
| 6,172,005 B1 | 1/2001 | Selby |
| 6,265,588 B1 | 7/2001 | Mullner et al. |
| 6,313,127 B1 | 11/2001 | Waterson et al. |
| 6,492,368 B1 | 12/2002 | Dorsch et al. |
| 6,511,977 B1 | 1/2003 | Lloyd et al. |
| 6,818,631 B1 | 11/2004 | Nakagawa et al. |
| 7,288,554 B2 | 10/2007 | Finkelstein et al. |
| 7,524,848 B2 | 4/2009 | Powers et al. |
| 7,572,913 B2 | 8/2009 | McKerracher et al. |
| 7,615,553 B2 | 11/2009 | Van Emelen et al. |
| 7,863,444 B2 | 1/2011 | Calderwood et al. |
| 8,058,313 B2 | 11/2011 | Reddy et al. |
| 8,642,660 B2 | 2/2014 | Goldfarb |
| 8,742,119 B2 | 6/2014 | Salituro et al. |
| 2003/0082877 A1 | 5/2003 | Ootsuka et al. |
| 2003/0095958 A1 | 5/2003 | Bhisetti et al. |
| 2003/0106381 A1 | 6/2003 | Krouth et al. |

(Continued)

FOREIGN PATENT DOCUMENTS

| | | |
|---|---|---|
| CA | 2235621 A1 | 5/1997 |
| CN | 101296909 A | 10/2008 |

(Continued)

OTHER PUBLICATIONS

Conti et al. Bollettino Scientifico della Facolta di Chimica Industriale di Bologna (1957), 15, 33-6.*
Luo et al. Nongyao (2009), 48(1), 19-22.*
Web posting, Pyruvate kinase M2 isozyme (PKM2), SciBX 5(42), Published online Oct. 25 2012, Abstract only.
Written Opinion of the International Searching Authority for PCT/US2008/009828, dated Dec. 5, 2008.
Yamada and Noguchi, "Nutrient and Hormonal Regulation of Pyruvate Kinase Gene Expression," Biochem J. 337: 1-11 (1999).
Yan et al., "IDH1 and IDH2 Mutations in Gliomas." The New England Journal of Medicine, 19 Feb. 18-22, 2009, vol. 360, No. 8, pp. 765-773.

(Continued)

*Primary Examiner* — Kahsay Habte
(74) *Attorney, Agent, or Firm* — Lando & Anastasi, LLP

(57) ABSTRACT

Compounds and compositions comprising compounds that activate pyruvate kinase M2 (PKM2) are described herein. Also described herein are methods of using the compounds that activate PKM2 in the treatment of cancer.

29 Claims, No Drawings

(56) References Cited

U.S. PATENT DOCUMENTS

| | | |
|---|---|---|
| 2003/0158232 A1 | 8/2003 | Cheng et al. |
| 2003/0187001 A1 | 10/2003 | Calderwood et al. |
| 2003/0207882 A1 | 11/2003 | Stocker et al. |
| 2004/0048283 A1 | 3/2004 | Pau et al. |
| 2004/0152648 A1 | 8/2004 | Ullrich et al. |
| 2004/0198979 A1 | 10/2004 | Dhanak et al. |
| 2004/0235755 A1 | 11/2004 | Eigenbrodt et al. |
| 2005/0176675 A1 | 8/2005 | Gorny |
| 2007/0032418 A1 | 2/2007 | Shapiro et al. |
| 2007/0127505 A1 | 6/2007 | Laurila et al. |
| 2007/0280918 A1 | 12/2007 | Schwartz et al. |
| 2008/0004269 A1 | 1/2008 | Xu et al. |
| 2008/0021116 A1 | 1/2008 | Ullrich et al. |
| 2008/0044833 A1 | 2/2008 | Connors |
| 2008/0051414 A1 | 2/2008 | Hurley et al. |
| 2009/0048227 A1 | 2/2009 | Chakravarty et al. |
| 2009/0054453 A1 | 2/2009 | Alcaraz et al. |
| 2009/0163545 A1 | 6/2009 | Goldfarb |
| 2009/0247499 A1 | 10/2009 | Fletcher et al. |
| 2009/0270454 A1 | 10/2009 | Weingarten et al. |
| 2010/0105657 A1 | 4/2010 | Nordvall et al. |
| 2010/0179150 A1 | 7/2010 | Basarab et al. |
| 2010/0331307 A1 | 12/2010 | Salituro et al. |
| 2011/0046083 A1 | 2/2011 | Cantley et al. |
| 2011/0224252 A1 | 9/2011 | Dumeunier et al. |
| 2011/0312931 A1 | 12/2011 | Cioffi et al. |

FOREIGN PATENT DOCUMENTS

| | | |
|---|---|---|
| DE | 3813886 A1 | 11/1989 |
| DE | 19841985 A1 | 3/2000 |
| EP | 0246749 A2 | 11/1987 |
| EP | 0628551 A1 | 12/1994 |
| EP | 1586558 A2 | 10/2005 |
| FR | 2735127 A1 | 12/1996 |
| GB | 1274436 A | 5/1972 |
| IT | 1176770 B | 8/1987 |
| JP | S61129129 A | 6/1986 |
| JP | 06-025177 | 2/1994 |
| JP | H07165708 A | 6/1995 |
| JP | 2002-193710 A | 7/2002 |
| JP | 2007/238458 A | 9/2007 |
| JP | 2008514590 A | 5/2008 |
| WO | 8501289 A1 | 3/1985 |
| WO | 9211761 A1 | 7/1992 |
| WO | 93/13072 A1 | 7/1993 |
| WO | 9630343 A1 | 10/1996 |
| WO | 97/28128 A1 | 8/1997 |
| WO | 97/28129 A1 | 8/1997 |
| WO | 97/28141 A1 | 8/1997 |
| WO | 9744322 A1 | 11/1997 |
| WO | 98/03350 A1 | 1/1998 |
| WO | 99/16751 A1 | 4/1999 |
| WO | 9916751 A1 | 4/1999 |
| WO | 0017202 A1 | 3/2000 |
| WO | 00/53596 A2 | 9/2000 |
| WO | 01/07440 A1 | 2/2001 |
| WO | 0119788 A2 | 3/2001 |
| WO | 0119798 A2 | 3/2001 |
| WO | 0164642 A2 | 9/2001 |
| WO | 0164643 A2 | 9/2001 |
| WO | 02/072077 A2 | 9/2002 |
| WO | 02/095063 A1 | 11/2002 |
| WO | 02100822 A1 | 12/2002 |
| WO | 0322277 A1 | 3/2003 |
| WO | 03037252 A2 | 5/2003 |
| WO | 03/062235 A1 | 7/2003 |
| WO | 03/073999 A2 | 9/2003 |
| WO | 03/076422 A1 | 9/2003 |
| WO | 03093297 A2 | 11/2003 |
| WO | 2004/004730 A2 | 1/2004 |
| WO | 2004014851 A2 | 2/2004 |
| WO | 2004/037251 A1 | 5/2004 |
| WO | 2004/073619 A2 | 9/2004 |
| WO | 2004/074438 A2 | 9/2004 |
| WO | 2004089470 A2 | 10/2004 |
| WO | 2004/110375 A2 | 12/2004 |
| WO | 2005/072642 A1 | 8/2005 |
| WO | 2005/117591 A2 | 12/2005 |
| WO | 2005120474 A2 | 12/2005 |
| WO | 2006/004195 A1 | 1/2006 |
| WO | 2006/016062 A1 | 2/2006 |
| WO | 2006033628 A1 | 3/2006 |
| WO | 2006034341 A2 | 3/2006 |
| WO | 2006-038594 A1 | 4/2006 |
| WO | 2006043950 A1 | 4/2006 |
| WO | 2006052190 A1 | 5/2006 |
| WO | 2006070198 A1 | 7/2006 |
| WO | 2006077821 A1 | 7/2006 |
| WO | 2006/122546 A1 | 11/2006 |
| WO | 2006117762 A2 | 11/2006 |
| WO | 2007003934 A2 | 1/2007 |
| WO | 2007023186 A1 | 3/2007 |
| WO | 2007117465 A2 | 10/2007 |
| WO | 2007/127505 A2 | 11/2007 |
| WO | 2008/019139 A2 | 2/2008 |
| WO | 2008024284 A2 | 2/2008 |
| WO | 2008/026658 A1 | 3/2008 |
| WO | 2008047198 A1 | 4/2008 |
| WO | 2008/050168 A1 | 5/2008 |
| WO | 2008052190 A2 | 5/2008 |
| WO | 2008073670 A2 | 6/2008 |
| WO | 2009012430 A1 | 1/2009 |
| WO | 2009013126 A1 | 1/2009 |
| WO | 2009/025781 A1 | 2/2009 |
| WO | 2009/053102 A1 | 4/2009 |
| WO | 2009086303 A2 | 7/2009 |
| WO | 2010/042867 A2 | 4/2010 |
| WO | 2010105243 A1 | 9/2010 |
| WO | 2010118063 A2 | 10/2010 |
| WO | 2010/129596 A1 | 11/2010 |
| WO | 2010130638 A1 | 11/2010 |
| WO | 2011002816 A1 | 1/2011 |
| WO | 2011002817 A1 | 1/2011 |
| WO | 2011032169 A2 | 3/2011 |
| WO | 2011047432 A1 | 4/2011 |
| WO | 2011/072174 A1 | 6/2011 |
| WO | 2011137089 A1 | 11/2011 |
| WO | 2012/092442 A1 | 7/2012 |

OTHER PUBLICATIONS

Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47 (20),3784-3786 (2008).

Ye et al., Pyruvate kinase M2 promotes de novo serine synthesis to sustain mTORC1 activity and cell proliferation, PNAS 109(18), 2012, pp. 6904-6909.

Adveenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.

Balss, "Analysis of the IDH1 codon 132 mutation in brain tumors", Acata Neuropathol (2008) vol. 116, pp. 597-602.

Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970, pp. 850-853.

Behun et al., "The Chemistry of Pyrazine and Its Derivatives. IV. The Alkylation and Arylation of Methylpyrazine," J Org. Chern., 26 (9),3379-3382 (1961).

Benesch et al., "The clinicopathological and prognostic relevance of pyruvate kinase M2 and pAkt expression in breast cancer." Anticancer Res.;30(5):1689-94 (2010).

Berger, et. al., "Treatment of Pancreatic Cancer: Challenge of the Facts" World J. Surg., Societe Internationale de Chirurgie, vol. 27, pp. 1075-1083, 2003.

Bonuccelli et al., "The reverse Warburg effect: Glycolysis inhibitors prevent the tumor promoting effects of caveolin-1 deficient cancer associated fibroblasts." Cell Cycle.;9(10) (2010).

(56) References Cited

OTHER PUBLICATIONS

Boxer, et al., "Evaluation of Substituted N,N?-Diarylsulfonamides as Activators of the Tumor Cell Specific M2 Isoform of Pyruvate Kinase", J Med Chem. Feb. 11, 2010; 53(3): 1048.

Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).

Budinger et al., "Cellular Energy Utilization and Supply During Hypoxia in Embryonic Cardiac Myocytes," Am J Physiol. 270: L44-53 (1996).

Buschow et al., "MHC class II-associated proteins in B-cell exosomes and potential functional implications for exosome biogenesis." Immunol Cell Biol. (2010).

Cecil Textbook of Medicine, edited by Bennet, J.C., and Plum F., 20th edition, vol. 1, 1004-1010, 1996.

Chabner, et. al., "Chemotherapy and the war on cancer", Nature Rev. Cancer, Nature Publishing Group, vol. 5, pp. 65-72, 2005.

Chan et al., "Synthesis and characterization of poly(amide sulfonamide)s (PASAs)," J Polymer. Sci., 33 (15), 2525-2531 (1995).

Christofk et al., "Pyruvate Kinase M2 is a Phosphotyrosine-Binding Protein," Nature 452: 181-186 (2008).

Christofk et al., "The M2 Splice Isoform of Pyruvate Kinase is Important for Cancer Metabolism and Tumour Growth," Nature 452: 230-233 (2008).

Clement, et. al., "Production of Intracellular Superoxide Mediates Dithiothreitol-Dependent Inhibition of Apoptotic Cell Death" Antioxidants and Redox Signaling, Mary Ann Liebert, vol. 7, issues 3-4, pp. 456-464, 2005.

Cohen et al., "The development and therapeutic potential of protein kinase inhibitors", Current Opinion in Chemical Biology, 3,459-465, 1999.

Cuzick, et. al., "Overview of the main outcomes in breast-cancer prevention trials" The Lancet, The Lancet Publishing Group, vol. 361, pp. 296-300, 2003.

Database Chemcats, Chemical Abstracts Service, Columbus, OH, US "Bionet Screening Compounds" Key Organics Ltd., Camelford, Cornwall (2001).

Dermer et al., "Another Anniversary for the War on Cancer", Bio/Technology, 1994, 12:320.

Dombrauckas, et al., Structural Basis for Tumor Pyruvate Kinasa M2 Allosteric Regulation and Catalysis, Biochemistry, vol. 44, p. 9717-9429 (2005).

Eigenbrodt et al., "Double Role for Pyruvate Kinase Type M2 in the Expansion of Phosphometabolite Pools Found in Tumor Cells," Crit Rev Oncog. 3: 91-115 (1992).

Engelman et al., "Allelic Dilution Obscures Detection of a Biologically Significant Resistance Mutation in EGFR-Amplified Lung Cancer," J Clin Invest. 116: 2695-2706 (2006).

Eswaran et al., "Crystal Structures and Inhibitor Identification for PTPN5, PTPRR and PTPN7: A Family of Human MAPK-Specific Protein Tyrosine Phosphatases," Biochem J. 395: 483-491 (2006).

Extended European Search Report (European Application No. 07836571.5), Dated Sep. 29, 2010.

Fabbro et al. "Protein kinases as targets for anticancer agents: from inhibitors to useful drugs." Pharmacology & Therapeutics 93, 79-98, 2002.

Freshney et al.,Culture of Animal Cells, A Manual of Basic Technique, Alan R. Liss, Inc., 1983, New York, p. 4.

Friedman et al., "Leptin and the regulation of body weight in mammals" Nature. vol. 395, 1996.

Furuya et al., Inactivation of the 3-phosphoglycerate dehydrogenase gene in mice: changes in gene expression and associated regulatory networks resulting from serine deficiency. Funct Integr Genomics (2008) 8:235-249.

Ge et al. "Anaplasma phagocytophilum inhibits human neutrophil apoptosis via upregulation of bfl-1, maintenance of mitochondrial membrane potential and prevention of caspase 3 activation." Cellular Microbilogy, 2005, 7(1 ), 29-38.

Golub et al., "Molecular Classification of Cancer: Class Discovery and Class Prediction by Gene Expression Monitoring", Science, 286, 531-537, 1999.

Gupta et al., "Dominant negative mutations affect oligomerisation of human pyruvate kinase M2 isozyme and promote cellular growth and polyploidy." J Biol Chem. (2010).

Hitosugi T et al: "Tyrosine Phosphorylation Inhibits PKM2 to Promote the Warburg Effect and Tumor Growth" Science Signaling, American Association for the Advancement of Science, US LNKD-DOI:10.1126/SCISIGNAL.2000431, vol. 2, No. 97, Nov. 17, 2009, pp. RA73-1.

Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.

Hulleman, et al., "Pyruvate kinase M2 and prednisolone resistance in acute lymphoblastic leukemia." Haematologica. Sep. 2009; 94(9): 1322-1324.

Inglese et al., "Quantitative high-throughput screening: A titration-based approach that efficiently identifies biological activities in large chemical libraries," Proc. Natl. Acad. Sci., 103 (31), 11473-11478 (2006).

International Preliminary Report for related application No. PCT/US2010/059778 dated Jun. 21, 2012.

International Preliminary Report for related application No. PCT/US2011/067752 dated Apr. 11, 2013.

International Preliminary Report on patentability for International Application No. PCT/US2007/017519, mailed Jul. 8, 2008.

International Preliminary Report on Patentability for PCT/US2008/009828, dated Feb. 16, 2010.

International Preliminary Report on Patentability for PCT/US2010/040489 dated Jan. 12, 2012.

International Preliminary Report on Patentability, Application No. PCT/US2009/060237, dated Apr. 12, 2011.

International Search Report & Written Opinion for PCT/US10/030139 dated Dec. 10, 2010.

International Search Report & Written Opinion for PCT/US10/40485 dated Aug. 11, 2010.

International Search Report and the Written Opinion of the International Search Authority (PCT/US07/17519), mailed Jul. 8, 2008.

International Search Report dated Apr. 4, 2012 for related Application PCT/US2011/065633.

International Search Report dated Mar. 5, 2012 for related international application No. PCT/US2011/067752.

International Search Report dated May 3, 2012 for related application PCT/US2011/066595.

International Search Report for Application No. PCT/US12/60099 dated Jan. 8, 2013.

Crawford et al., Caplus an 2010:1218943.

European Search report for EP Application No. 10 794 667.5 dated Oct. 9, 2013.

International Search Report for PCT/US2011/065633 dated Jun. 18, 2013.

Komoriya et al. "Design, synthesis, and biological activity of non-basic compounds as factor Xa inhibitors: SAR study of S1 and aryl binding sites" Bioorganic & Medicinal Chemistry 13 (2005) 3927-3954.

Patel et al. "Synthesis of some new idolinone derivatives containing piperazine moiety" Bulgarian Chemical Communications, 2003 Bol 35 No. 4 pp. 242-244.

Proisy et al. "Rapid Synthesis of 3-Aminoisoquinoline-5-sulfonamides Using the Buchwald-Hartwig Reaction" Synthesis 2009, No. 4, pp. 0561-0566.

Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.

International Search Report for PCT/US10/040486 dated Sep. 1, 2010.

International Search Report for PCT/US2008/009828, dated Dec. 5, 2008.

International Search Report for PCT/US2010/033610 dated Jul. 22, 10.

International Search Report for PCT/US2010/059778 dated Mar. 17, 2011.

(56) References Cited

OTHER PUBLICATIONS

International Search Report, Application No. PCT/US2009/060237, dated Jun. 16, 2010.
International Search Report, Application No. PCT/US2011/033852, dated Aug. 3, 2011.
Jiang et al., "Evaluation of thieno[3,2-b]pyrrole[3,2-d]pyridazinones as activators of the tumor cell specific M2 isoform of pyruvate kinase." Bioorg. Med. Chern. Lett., 20 (11), 3387-3393 (2010).
Joshi et al., "Age-related faecal calprotectin, lactoferrin and tumour M2-PK concentrations in healthy volunteers." Ann Clin Biochem. ;47(Pt 3):259-63 (2010).
Jurica et al., "The Allosteric Regulation of Pyruvate Kinase by Fructose-1,6-Bisphosphate," Structure 6: 195-210 (1998).
Kao et al., "A Small-Molecule Inhibitor of the Ribonucleolytic Activity of Human Angiogenin That Possesses Antitumor Activity," Proc. Natl. Acad. Sci. USA, 99(15): 10066-10071 (2002).
Kharalkar et al., "Identification of Novel Allosteric Regulators of Human-Erythrocyte Pyruvate Kinase," Chem Biodivers. 4: 2603-2617 (2007).
Klapars et al., "A General and Efficient Copper Catalyst for the Amidation of Aryl Halides and the N-Arylation of Nitrogen Heterocycles," J. Am. Chem. Soc., 123 (31), 7727-7729 (2001).
Kumar et al., "In vivo factors influencing tumour M2-pyruvate kinase level in human pancreatic cancer cell lines." Tumour Biol.;31(2):69-77 (2010).
Kung et al. "Small Molecule Activation of PKM2 in Cancer Cells Induces Serine Auxotrophy" Chemistry & Biology, 19, 1187-1198, Sep. 21, 2012.
Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).
Lee, "Consolidation Effect of Phenylalanine-administration of Antitumor Activity of a 5 Fluorouracil," Med. J. Kagoshima Univ. 37(3-4): 285-308 (1985).
Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.
Li et al., "Quantitative proteome analysis of multidrug resistance in human ovarian cancer cell line." J Cell Biochem.;109(4):625-33 (2010).
Li et al., "Screening and identification of interactive proteins of SH2D4A." Yi Chuan.;32(7):712-8 (2010). (Abstract Only).
Mass, R. D., "The HER receptor family: a rich target for therapeutic development", Int. J. Radiation Oncology Bio. Phys. vol. 58(3): 932-940, 2004.
Oeda, "On some 2,5-Dialikl-piperazines," Bull. Chem. Soc., 13, 465-470 (1938).
Park, "Prevention of type 2 diabetes mellitus from the viewpoint of genetics." Diabetes Research and Clinical Practice 2004; 66S: S33-S35.
Paudler et al., "3,7-Disubstituted octahydro-1,5-diazocines. Their conversion into tetrahydro-1,5-diazocines and into ring-contracted products," J. Org. Chern., 32 (8), 2425-2430 (1967).
Pollard et al., "Some Amides of Piperazines," J. Am. Chem. Soc., 75 (2), 491 (1953).
Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.
Remington's, "Structure Activity Relationship and Drug Design," Pharmaceutical Sciences, pp. 420-425p. 420-425, 1980.
Rich, et. al., "Development of novel targeted therapies in the treatment of malignant glioma" Nature Rev. Drug Disc., Nature Publishing Group, vol. 3, pp. 430-446, 2004.
Root et al., "Genome-Scale Loss-of-Function Screening with a Lentiviral RNAi Library," Nat Methods 3: 715-719 (2006).
Ruan et al., "HSP60, a protein downregulated by IGFBP7 in colorectal carcinoma." J Exp Clin Cancer Res.;29:41 (2010).

Sabatine et al., "Metabolomic Identification of Novel Biomarkers of Myocardial Ischemia," Circulation 112: 3868-3875 (2005).
Schneider, et. al., "Tumor M2-pyruvate kinase in the follow-up of inoperable lung cancer patients: a pilot study." Cancer Letters, Elsevier, vol. 193, pp. 91-98, 2003.
Schroth et al., "RingschluBreaktion von Diacetylen mit Diaminen: Eine Ciniache von 2,3-Dihydro-1,4-diazepinen," Zeitschritt Fur Chemie., 6 (4), 143 (1969).
Seibel et al., "Synthesis and evaluation of B-lactams (piperazones) as elastase inhibitors," Bioorg. Med. Chern. Ltrs., 13 (3),387-389 (2003).
Shi, et al., "Silencing of pkm2 increases the efficacy of docetaxel in human lung cancer xenografts in mice." Cancer Science, vol. 101, # 6, 1447-1453, Jun. 2010.
Stewart et al., "Piperazines. I. Derivatives of Piperazine-1-Carboxylic and -1,4-Dicarboxylic Acid,", J. Org. Chern., 18 (1),1478-1483 (1953).
STN File CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
Supplemental EP Search Report & Written Opinion for EP 10 79 4667 dated Jan. 15, 2013.
Supplementary Search Report for EP10794668 Mailed Oct. 18, 2012.
Surh, "Cancer Chemoprevention with Dietary Phytochemicals", Nature Reviews Cancer, Nature Publishing Group, vol. 3, p. 768-780, 2003.
Szoka et al., "Comparative properties and methods of preparation of lipid vesicles (liposomes)," Ann. Rev. Biophys. Bioeng., 9, 467-508 (1980).
Uozumi et al., "Catalytic asymmetric construction of morpholines and piperazines by palladium-catalyzed tandem allylic substitution reactions," J. Org. Chem, 58 (24),6826-6832 (1993).
Vander Heiden et al., "Growth Factors Can Influence Cell Growth and Survival Through Effects on Glucose Metabolism," Mol Cell Bioi. 21: 5899-5912 (2001).
Vander Heiden et al., "Identification of Small Molecule Inhibitors of Pyruvate Kinase M2," Biochemical Pharmacology. 79(8): 1118-1124 (2010).
Villen et al., "Large-Scale Phosphorylation Analysis of Mouse Liver," Proc Nat! Acad Sci USA 104: 1488-1493 (2007).
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.
Conti et al. "Su alcuni analoghi assigenati della benzo-tiazine 2-3-diidro-3-cheto-benzo-1-4-ossazine 6-sostitute" Bollettino Scientifico Della Facolta Di Chimica Industriale Di Bologna (1957) vol. XV, No. 2, pp. 33-36.
European Search Report for European Application No. 11808773.3 dated Apr. 9, 2014.
European Search Report for European Application No. 11811257.2 dated Apr. 23, 2014.
STN File CA, Registry No. 321433-63-0, entered STN on Feb. 12, 2001, Chemical Abstracts Index Name "1H-Pyrrole-2-sulfonamide, 1-[3-chloro-5-(trifluoromethyl)-2-pyridinyl]-N-phenyl" Available though Key Organics (under the BIONET brand) Jan. 1994.

(56) References Cited

OTHER PUBLICATIONS

STN File CA, Registry No. 321433-64-1, entered STN on Feb. 12, 2001, Chemical Abstracts Index Name "1H-Pyrrole-2-sulfonamide, 1-[3-chloro-5-(trifluoromethyl)-2-pyridinyl]-N-(4-methphenyl)" Available though Key Organics (under the Bionet brand) Jan. 1994.

STN File CA, Registry No. 321433-65-2, entered STN on Feb. 12, 2001, Chemical Abstracts Index Name "1H-Pyrrole-2-sulfonamide, 1-[3-chloro-5-(trifluoromethyl)-2-pyridinyl]-N-(3,5-dimethylphenyl)" Available though Key Organics (under the BIONET brand) Jan. 1994.

STN File CA, Registry No. 321433-66-3, entered STN on Feb. 12, 2001, Chemical Abstracts Index Name "1H-Pyrrole-2-sulfonamide, 1-[3-chloro-5-(trifluoromethyl)-2-pyridinyl]-N-(4-methoxyphenyl)" Available though Key Organics (under the BIONET brand) Jan. 1994.

STN File CA, Registry No. 321433-68-5, entered STN on Feb. 12, 2001, Chemical Abstracts Index Name "1H-Pyrrole-2-sulfonamide, 1-[3-chloro-5-(trifluoromethyl)-2-pyridinyl]-N-propyl" Available though Key Organics (under the BIONET brand) Jan. 1994.

STN File CA, Registry No. 321433-69-6, entered STN on Feb. 12, 2001, Chemical Abstracts Index Name "1H-Pyrrole-2-sulfonamide, 1-[3-chloro-5-(trifluoromethyl)-2-pyridinyl]-N-(2-methoxyethyl)" Available though Key Organics (under the BIONET brand) Jan. 1994.

STN File CA, Registry No. 338397-92-5, entered STN on May 25, 2001, Chemical Abstracts Index Name "1H-Pyrrole-2-sulfonamide, 1-[3-chloro-5-(trifluoromethyl)-2-pyridinyl]-N,N-dimethyl" Available though Key Organics (under the BIONET brand) Feb. 1993.

STN File CA, Registry No. 338397-95-8, entered STN on May 25, 2001, Chemical Abstracts Index Name "1H-Pyrrole-2-sulfonamide, N-[(4-chlorophenyl)-1-[3-chloro-5-(trifluoromethyl)-2-pyridinyl]" Available though Key Organics (under the BIONET brand) Feb. 1993.

STN File CA, Registry No. 338397-96-9, entered STN on May 25, 2001, Chemical Abstracts Index Name "1H-Pyrrole-2-sulfonic acid, 1-[3-chloro-5-(trifluoromethyl)-2-pyridinyl]-4-chlorophenyl ester" Available though Key Organics (under the BIONET brand) Feb. 1993.

STN File CA, Registry No. 338406-58-9, entered STN on May 25, 2001, Chemical Abstracts Index Name "1H-Pyrrole-2-sulfonamide, 1-[3-chloro-5-(trifluoromethyl)-2-pyridinyl]-N-[2-(trifluoromethyl)phenyl]" Available though Key Organics (under the BIONET brand) Mar. 1993.

STN File CA, Registry No. 338406-64-7, entered STN on May 25, 2001, Chemical Abstracts Index Name "1H-Pyrrole-2-sulfonamide, 1-[3-chloro-5-(trifluoromethyl)-2-pyridinyl]-N-(3-pyridinylmethyl)" Available though Key Organics (under the BIONET brand) Mar. 1993.

STN File CA, Registry No. 338406-72-7, entered STN on May 25, 2001, Chemical Abstracts Index Name "1H-Pyrrole-2-sulfonamide, N-[(4-chlorophenyl)methyl]-1-[3-chloro-5-(trifluoromethyl)-2-pyridinyl]" Available though Key Organics (under the BIONET brand) Mar. 1993.

STN File CA, Registry No. 338407-11-7, entered STN on May 25, 2001, Chemical Abstracts Index Name "1H=Pyrrole-2-sulfonamide, 1-[3-chloro-5-(trifluoromethyl)-2-pyridinyl]-N-[3-chloro-4-[[5-(trifluoromethyl)-2-pyridinyl]oxy] phenyl]" Available though Key Organics (under the BIONET brand) Mar. 1993.

STN File CA, Registry No. 338407-13-9, entered STN on May 25, 2001, Chemical Abstracts Index Name "Benzoic acid, 3-[[[1-[3-chloro-5-(trifluoromethyl)-2-pyridinyl]-1H-pyrrol-2-yl]sulfonyl]amino]" Available though Key Organics (under the BIONET brand) Mar. 1993.

Supplemental EP Search Report for European Application No. 10714131.9 dated Oct. 17, 2014.

Wong et al. "PKM2, a Central Point of Regulation in Cancer Metabolism" International Journal of Cell Biology (2013) vol. 2013, pp. 1-11.

Morshed et al. "Computational approach to the identification of novel Aurora-A inhibitors" Bioorganic & Medicinal chemistry (2011) vol. 19, No. 2, pp. 907-916.

STN Tokyo, Registry No. 1001833-18-6, Entered STN on Feb. 6, 2008, Chemical Abstracts Index Name "1,4-Benzodioxin-6-sulfonamide, 2,3-dihydro-N-[4-[(4-methyl-l-piperazinyl)carbonyl]phenyl]-".

STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5-methyl-3-isoxazolyl)methyl]-l-piperazinyl]carbonyl]phenyl]-".

STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".

STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2-pyridinyl)-l-piperazinyl]carbonyl]phenyl]-".

STN Tokyo, Registry No. 1240875-006, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".

STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro-".

STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".

STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".

STN Tokyo, Registry No. 878590-33-1, Entered STN on Mar. 30, 2006, Chemical Abstracts Index Name "1,4-Benzodioxin-6-sulfonamide, 2,3-dihydro-N-[4{{4-(tetrahydro-2-furanyl)methyl]-1-piperazinyl]carbonyl]phenyl]-".

STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".

STN Tokyo, Registry No. 878956-06-0, Entered STN on Apr. 2, 2006, Chemical Abstracts Index Name "1,4-Benzodioxin-6-sulfonamide, N-[4-[[4-(cyclopropylcarbonyl)-1-piperazinyl]carbonyl]phenyl]-2,3-dihydro-".

STN Tokyo, Registry No. 9200679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]".

STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro-".

STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]-".

STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]-".

STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]-".

STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-l-piperazinyl]carbonyl]phenyl]-".

(56) References Cited

OTHER PUBLICATIONS

STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".

STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]-".

STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-l-piperazinyl)carbonyl]phenyl]-".

Tawaka, et al., Caplus an 1998:794998 (1998).

Villoutreix et al., Caplus an 2010:20993 (2010).

\* cited by examiner

BICYCLIC PKM2 ACTIVATORS

CLAIM OF PRIORITY

This application is a national stage application under 35 U.S.C. §371 of International Application No. PCT/US2011/066595, filed Dec. 21, 2011, and published as International Publication No. WO 2012/088314 on Jun. 28, 2012, which claims priority from U.S. Ser. No. 61/425,557, filed Dec. 21, 2010, U.S. Ser. No. 61/425,499, filed Dec. 21, 2010, U.S. Ser. No. 61/425,513, filed Dec. 21, 2010, and U.S. Ser. No. 61/425,528, filed Dec. 21, 2010; the content of each of these applications is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Thus, the modulation (e.g., activation) of PKM2 may be effective in the treatment of, e.g., obesity, diabetes, autoimmune conditions, and proliferation-dependent diseases, e.g., benign prostatic hyperplasia (BPH). Current modulators of pyruvate kinase are not selective, making it difficult to treat disease related to pyruvate kinase function.

Furthermore, phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 can also inhibit the growth and proliferation of cancer cells, activated immune cells, and fat cells.

There is a continuing need for novel treatments of diseases such as cancer, diabetes, obesity, autoimmune conditions, proliferation-dependent diseases (e.g., BPH), and other diseases related to the function of pyruvate kinase (e.g., PKM2).

SUMMARY OF INVENTION

Described herein are compounds that modulate pyruvate kinase M2 (PKM2) and pharmaceutically acceptable salts thereof, for example, compounds that activate PKM2. This invention also provides compositions and pharmaceutical kits comprising a compound of this invention and the use of such compositions and kits in methods of treating diseases and conditions that are related to pyruvate kinase function (e.g., PKM2 function), including, e.g., cancer, diabetes, obesity, autoimmune disorders, and benign prostatic hyperplasia (BPH).

In one aspect, the present invention is directed to a compound of formula (I),

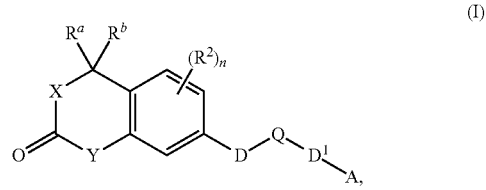

wherein

X and Y are each independently selected from O and N(-L-$R^1$);

Q is C(O), $SO_2$, or —$(CH_2)_h$—;

each L is independently selected from a bond, —C(O)—, —$(CR^aR^b)_m$—, —C(O)N($R^c$)— or —C(O)O—;

D and $D^1$ are each independently selected from a bond, O and N($R^c$), provided that D and $D^1$ are not both a bond;

A is aryl or heteroaryl, each of which is substituted with 0-3 occurrences of $R^d$; and D-Q-$D^1$-A is not $OCH_2$-phenyl;

each $R^1$ is independently selected from hydrogen, $C_{1-4}$ alkyl, halo $C_{1-4}$alkyl, alkyl-O-alkylene, $C_{3-10}$ cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$;

each $R^a$ and each $R^b$ are independently selected from hydrogen, $C_{1-4}$ alkyl, or $R^a$ and $R^b$ bound to the same carbon atom are taken together with the carbon atom to form a cycloalkyl;

each $R^c$ is independently selected from hydrogen and $C_{1-4}$ alkyl;

each $R^d$ is independently selected from halo, halo $C_{1-4}$ alkyl, $C_{1-4}$ alkyl, nitro, cyano, —OH and —O($C_{1-4}$ alkyl), or two $R^d$, attached to the same or adjacent carbon atoms, taken together with the atom(s) to which they are attached form an optionally substituted heterocyclyl;

each $R^f$ is independently selected from halo, halo $C_{1-4}$alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl;

h is 1, 2 or 3;

each m is independently 1, 2 or 3; and each n is independently 0, 1, 2 or 3;

provided that the compound is not 2-chloro-N-(1,4-dihydro-2-oxo-2H-3,1-benzoxazin-7-yl)-5-[[(1-methylethyl)amino]sulfonyl]-benzamide;

4-[2-oxo-7-(phenylmethoxy)-2H-1,3-benzoxazin-3 (4H)-yl], Benzoic methyl ester;

2-chloro-5-[[(1-methylethyl)amino]sulfonyl]-N-(1,2,3,4-tetrahydro-2-oxo-7-quinazolinyl)-benzamide; or 2-chloro-5-[[(1-methylethyl)amino]sulfonyl]-N-(1,2,3,4-tetrahydro-3-methyl-2-oxo-7-quinazolinyl)-benzamide.

In certain embodiments of Formula (I), D is a bond.

In some embodiments of Formula (I), D is N($R^c$). In one aspect of these embodiments of Formula (I), $R^c$ is hydrogen.

In certain embodiments of Formula (I), D is a bond and $D^1$ is N($R^c$). In one aspect of these embodiments of Formula (I), Q is $SO_2$. In another aspect of these embodiments of Formula (I), Q is C(O). In a more particular aspect of these embodiments of Formula (I), $D^1$ is NH and Q is C(O). In another aspect of these embodiments of Formula (I), Q is $(CH_2)_h$. In a more particular aspect of these embodiments of Formula (I), Q is $CH_2$. In another more particular aspect of these embodiments of Formula (I), $D^1$ is NH and Q is $(CH_2)_h$. In an even more particular aspect of these embodiments of Formula (I), $D^1$ is NH and Q is $CH_2$.

In some embodiments of Formula (I), $D^1$ is oxygen.

In some embodiments of Formula (I), D is a bond and $D^1$ is oxygen. In one aspect of these embodiments of Formula (I), Q is C(O).

In some embodiments of Formula (I), D is oxygen. In one aspect of these embodiments of Formula (I), Q is C(O) and $D^1$ is N($R^c$).

In some embodiments of Formula (I), $D^1$ is N($R^c$). In one aspect of these embodiments of Formula (I), D is NH. In another aspect of these embodiments of Formula (I), Q is C(O) and D is oxygen.

In certain embodiments of Formula (I), Q is $SO_2$.

In some embodiments of Formula (I), Q is $(CH_2)_h$. In one aspect of these embodiments of Formula (I), h is 1.

In some embodiments of Formula (I), Q is C(O).

In certain embodiments of Formula (I), $R^a$ is hydrogen.

In certain embodiments of Formula (I), $R^b$ is hydrogen.

In another aspect, the present invention is directed to a compound of Formula (I), wherein D is a bond, Q is $S(O)_2$, and $D^1$ is —NH—, the compound having the formula (Ia):

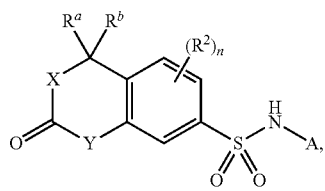

(Ia)

wherein X, Y, L, $R^a$, $R^b$, $R^c$, $R^d$, $R^f$, $R^g$, $R^1$, $R^2$, A, n and m are as described above for Formula (I).

The following embodiments and aspects thereof relate to both Formula (I) and Formula (Ia).

In some embodiments of Formulas (I) and (Ia), Y is N-L-$R^1$.

In certain embodiments of Formulas (I) and (Ia), Y is N-L-$R^1$ and L is a bond. In one aspect of these embodiments of Formulas (I) and (Ia), $R^1$ is hydrogen. In still another aspect of these embodiments of Formulas (I) and (Ia), $R^1$ is $C_{1-4}$ alkyl substituted with 0-3 occurrences of $R^g$. In a more specific aspect of these embodiments of Formulas (I) and (Ia), $R^1$ is $C_{1-4}$ alkyl substituted with 0 occurrences of $R^g$ (e.g., methyl).

In certain embodiments of Formulas (I) and (Ia), Y is N-L-$R^1$ and L is —$(CR^aR^b)_m$—. In a specific aspect of these embodiments of Formulas (I) and (Ia), L is —$CR^aR^b$— (e.g., m is 1). In an even more specific aspect of these embodiments of Formulas (I) and (Ia), L is —$CH_2$— (e.g, $R^a$ and $R^b$ are hydrogen). In another specific aspect of these embodiments of Formulas (I) and (Ia), $R^1$ is aryl substituted with 0-3 occurrences of $R^f$. In a more specific aspect of these embodiments of Formulas (I) and (Ia), $R^1$ is unsubstituted phenyl.

In certain embodiments of Formulas (I) and (Ia), X is O.

In certain embodiments of Formulas (I) and (Ia), X is O and Y is N-L-$R^1$.

In certain embodiments of Formulas (I) and (Ia), X is O, Y is N-L-$R^1$ and L is a bond. In one aspect of these embodiments of Formulas (I) and (Ia), $R^1$ is hydrogen. In still another aspect of these embodiments of Formulas (I) and (Ia), $R^1$ is $C_{1-4}$ alkyl substituted with 0-3 occurrences of $R^g$. In a more specific aspect of these embodiments of Formulas (I) and (Ia), $R^1$ is $C_{1-4}$ alkyl substituted with 0 occurrences of $R^g$ (e.g., methyl).

In certain embodiments of Formulas (I) and (Ia), X is O, Y is N-L-$R^1$ and L is —$(CR^aR^b)_m$—. In a specific aspect of these embodiments of Formulas (I) and (Ia), L is —$CR^aR^b$— (e.g., m is 1). In an even more specific aspect of these embodiments of Formulas (I) and (Ia), L is —$CH_2$— (e.g, $R^a$ and $R^b$ are hydrogen). In another specific aspect of these embodiments of Formulas (I) and (Ia), $R^1$ is aryl substituted with 0-3 occurrences of $R^f$. In a more specific aspect of these embodiments of Formulas (I) and (Ia), $R^1$ is unsubstituted phenyl.

In certain embodiments of Formulas (I) and (Ia), X is N-L-$R^1$.

In certain embodiments of Formulas (I) and (Ia), X is N-L-$R^1$, and L is a bond. In one aspect of these embodiments of Formulas (I) and (Ia), $R^1$ is hydrogen. In still another aspect of these embodiments of Formulas (I) and (Ia), $R^1$ is $C_{1-4}$ alkyl substituted with 0-3 occurrences of $R^g$. In a more specific aspect of these embodiments of Formulas (I) and (Ia), $R^1$ is $C_{1-4}$ alkyl substituted with 0 occurrences of $R^g$ (e.g., methyl).

In some embodiments of Formulas (I) and (Ia), X is N-L-$R^1$, and L is —$(CR^aR^b)_m$—. In a specific aspect of these embodiments of Formulas (I) and (Ia), L is —$CR^aR^b$— (e.g., m is 1). In an even more specific aspect of these embodiments of Formulas (I) and (Ia), L is —$CH_2$— (e.g, $R^a$ and $R^b$ are hydrogen). In another specific aspect of these embodiments of Formulas (I) and (Ia), $R^1$ is aryl substituted with 0-3 occurrences of $R^f$. In a more specific aspect of these embodiments of Formulas (I) and (Ia), $R^1$ is unsubstituted phenyl.

In some embodiments of Formulas (I) and (Ia), Y is O.

In some embodiments of Formulas (I) and (Ia), Y is O and X is N-L-$R^1$.

In certain embodiments of Formulas (I) and (Ia), X is N-L-$R^1$, Y is O and L is a bond. In one aspect of these embodiments of Formulas (I) and (Ia), $R^1$ is hydrogen. In still another aspect of these embodiments of Formulas (I) and (Ia), $R^1$ is $C_{1-4}$ alkyl substituted with 0-3 occurrences of $R^f$. In a more specific aspect of these embodiments of Formulas (I) and (Ia), $R^1$ is $C_{1-4}$ alkyl substituted with 0 occurrences of $R^f$ (e.g., methyl).

In some embodiments of Formulas (I) and (Ia), X is N-L-$R^1$, Y is O and L is —$(CR^aR^b)_m$—. In a specific aspect of these embodiments of Formulas (I) and (Ia), L is —$CR^aR^b$— (e.g., m is 1). In an even more specific aspect of these embodiments of Formulas (I) and (Ia), L is —$CH_2$— (e.g, $R^a$ and $R^b$ are hydrogen). In another specific aspect of these embodiments of Formulas (I) and (Ia), $R^1$ is aryl substituted with 0-3 occurrences of $R^f$. In a more specific aspect of these embodiments of Formulas (I) and (Ia), $R^1$ is unsubstituted phenyl.

In certain embodiments of Formulas (I) and (Ia), n is 0.

In some embodiments of Formulas (I) and (Ia), n is 1.

In certain embodiments of Formulas (I) and (Ia), A is aryl (e.g., monocyclic or bicyclic aryl) substituted with 0-3 occurrences of $R^d$. In one aspect of these embodiments of Formulas (I) and (Ia), A is 5-8 membered monocyclic aryl substituted with 0-3 occurrences of $R^d$. In a more specific aspect of these embodiments of Formulas (I) and (Ia), A is phenyl substituted with 0-3 occurrences of $R^d$. In an even more specific aspect of these embodiments of Formulas (I) and (Ia), A is phenyl substituted with 0 occurrences of $R^d$. In another even more specific aspect of these embodiments of Formulas (I) and (Ia), A is phenyl substituted with 1 occurrence of $R^d$.

In some aspects of embodiments of Formulas (I) and (Ia), when A is phenyl substituted with 1 occurrence of $R^d$, that $R^d$ is halo (e.g., A is p-fluorophenyl or m-chlorophenyl). In another aspect of these embodiments of Formulas (I) and (Ia), the $R^d$ substituent on A is alkyl (e.g., methyl or ethyl). In still another aspect of these embodiments of Formulas (I) and (Ia), the $R^d$ substituent on A is —$OR^a$ (e.g., p-substituted —$OR^a$). In some embodiments of Formulas (I) and (Ia), the $R^d$ substituent on A is alkoxy (e.g., methoxy).

In certain embodiments of Formulas (I) and (Ia), A is phenyl substituted with 2 occurrences of $R^d$. In one aspect of these embodiments of Formulas (I) and (Ia), both $R^d$ substituents on A are halo (e.g., 3-chloro-4-fluorophenyl). In another aspect of these embodiments of Formulas (I) and (Ia), both $R^d$ substituents on A are alkyl (e.g., 3,5-dimethylphenyl). In still another aspect of these embodiments of Formulas (I) and (Ia), one $R^d$ substituent on A is alkyl and the other is halo (e.g., 3-methyl-4-fluorophenyl). In yet another aspect of these embodiments of Formulas (I) and (Ia), two $R^d$ substituents on A, attached to the same or adjacent carbon atoms are taken together with the atoms to which they are attached form an optionally substituted heterocyclyl.

In another aspect, the present invention is directed to a compound of Formula

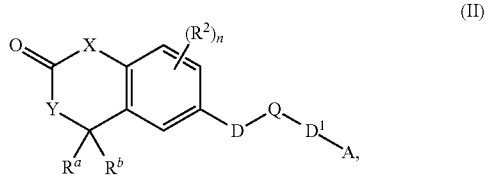

(II)

wherein

X and Y are each independently selected from O and N-L-$R^1$;

Q is C(O), $SO_2$, or —$(CH_2)_h$—;

each L is independently selected from a bond, —C(O)—, —$(CR^aR^b)_m$—, —C(O)$NR^c$— or —C(O)O—;

D and $D^1$ are each independently selected from a bond, O and $NR^c$, provided that D and $D^1$ are not both a bond;

A is aryl or heteroaryl, each of which is substituted with 0-3 occurrences of $R^d$;

each $R^1$ is independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$;

each $R^a$ and each $R^b$ are independently selected from hydrogen, $C_{1-4}$ alkyl, or $R^a$ and $R^b$ bound to the same carbon atom are taken together with the carbon atom to form a cycloalkyl;

each $R^c$ is independently selected from hydrogen and $C_{1-4}$ alkyl;

each $R^d$ is independently selected from halo, halo $C_{1-4}$ alkyl, $C_{1-4}$ alkyl, nitro, cyano, —OH and —O($C_{1-4}$ alkyl), or two $R^d$, attached to the same or adjacent carbon atoms, taken together with the atoms to which they are attached form an optionally substituted heterocyclyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl;

h is 1, 2 or 3;

each m is independently 1, 2 or 3; and each n is independently 0, 1, 2 or 3; provided that
1) D-Q-$D^1$-A is not i) O-benzyl, ii) $NHSO_2$-2-thiophenyl, iii) NHC(O)-optionally substituted phenyl, or iv) $NHSO_2$-optionally substituted phenyl; and
2) the compound is not:
   i) N-(2,6-dimethylphenyl)-1,2,3,4-tetrahydro-1,3-dimethyl-2-oxo-6-Quinazolinesulfonamide;
   ii) N-[2-[[[(1S)-2-cyclohexyl-1-methylethyl]amino]methyl]phenyl]-1,4-dihydro-2-oxo-2H-3,1-Benzoxazine-6-sulfonamide; or
   iii) N-[2-[[[(1S)-2-cyclopentyl-1-methylethyl]amino]methyl]phenyl]-1,4-dihydro-2-oxo-2H-3,1-Benzoxazine-6-sulfonamide.

In certain embodiments of Formula (II), D is a bond.

In some embodiments of Formula (II), D is $N(R^c)$. In one aspect of these embodiments of Formula (II), $R^c$ is hydrogen.

In certain embodiments of Formula (II), D is a bond and $D^1$ is $N(R^c)$. In one aspect of this embodiment of Formula (II), Q is $SO_2$. In another aspect of these embodiments of Formula (II), Q is $SO_2$ and $D^1$ is NH. In another aspect of these embodiments of Formula (II), Q is C(O). In a more particular aspect of these embodiments of Formula (II), $D^1$ is NH and Q is C(O). In another aspect of these embodiments of Formula (II), Q is $(CH_2)_h$. In a more particular aspect of these embodiments of Formula (II), Q is $CH_2$. In another more particular aspect of these embodiments of Formula (II), $D^1$ is NH and Q is $(CH_2)_h$. In an even more particular aspect of these embodiments of Formula (II), $D^1$ is NH and Q is $CH_2$.

In some embodiments of Formula (II), $D^1$ is oxygen.

In some embodiments of Formula (II), D is a bond and $D^1$ is oxygen. In one aspect of these embodiments of Formula (II), Q is C(O).

In some embodiments of Formula (II), D is $N(R^c)$ and $D^1$ is oxygen. In one aspect of these embodiments of Formula (II), Q is C(O). In a more particular aspect of these embodiments of Formula (II), D is NH and Q is C(O).

In some embodiments of Formula (II), D is oxygen. In one aspect of these embodiments of Formula (II), Q is C(O) and $D^1$ is $N(R^c)$. In a more particular aspect of these embodiments of Formula (II), Q is C(O) and $D^1$ is NH.

In certain embodiments of Formula (II), Q is $SO_2$. In some embodiments of Formula (II), Q is $(CH_2)_h$. In one aspect of these embodiments of Formula (II), h is 1.

In some embodiments of Formula (II), Q is C(O).

In certain embodiments of Formula (II), $R^a$ is hydrogen.

In certain embodiments of Formula (II), $R^b$ is hydrogen.

In another aspect, the present invention is directed to a compound of Formula (II), wherein D is a bond, Q is S(O)$_2$ and D$^1$ is —NH—, the compound having the formula (IIa):

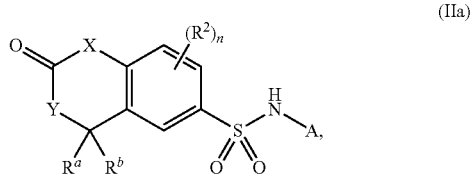

(IIa)

wherein X, Y, L, R$^a$, R$^b$, R$^c$, R$^d$, R$^f$, R$^g$, R$^1$, R$^2$, A, n and m are as described for formula (II).

The following embodiments and aspects thereof relate to both formula (II) and formula (IIa).

In certain embodiments of Formulas (II) and (IIa), Y is N-L-R$^1$.

In some embodiments of Formulas (II) and (IIa), Y is N-L-R$^1$ and L is a bond. In one aspect of these embodiments of Formulas (II) and (IIa), R$^1$ is hydrogen. In another aspect of these embodiments of Formulas (II) and (IIa), R$^1$ is C$_{1-4}$ alkyl substituted with 0-3 occurrences of R$^g$. In a more specific aspect of these embodiments of Formulas (II) and (IIa), R$^1$ is C$_{1-4}$ alkyl substituted with 0 occurrences of R$^g$ (e.g., methyl).

In some embodiments of Formulas (II) and (IIa), Y is N-L-R$^1$ and L is —(CR$^a$R$^b$)$_m$—. In a specific aspect of these embodiments of Formulas (II) and (IIa), L is —CR$^a$R$^b$— (e.g., m is 1). In a more specific aspect of these embodiments of Formulas (II) and (IIa), L is —CH$_2$— (e.g., R$^a$ and R$^b$ are hydrogen). In another aspect of these embodiments of Formulas (II) and (IIa), R$^1$ is aryl substituted with 0-3 occurrences of R$^f$. In a more specific aspect of these embodiments of Formulas (II) and (IIa), R$^1$ is aryl substituted with 0 occurrences of R$^f$. In an even more specific aspect of these embodiments of Formulas (II) and (IIa), R$^1$ is unsubstituted phenyl.

In certain embodiments of Formulas (II) and (IIa), X is O.

In certain embodiments of Formulas (II) and (IIa), X is O and Y is N-L-R$^1$.

In certain embodiments of Formulas (II) and (IIa), X is O, Y is N-L-R$^1$ and L is a bond. In one aspect of these embodiments of Formulas (II) and (IIa), R$^1$ is hydrogen. In another aspect of these embodiments of Formulas (II) and (IIa), R$^1$ is C$_{1-4}$ alkyl substituted with 0-3 occurrences of R$^g$. In a more specific aspect of these embodiments of Formulas (II) and (IIa), R$^1$ is C$_{1-4}$ alkyl substituted with 0 occurrences of R$^g$ (e.g., methyl).

In certain embodiments of Formulas (II) and (IIa), X is O and Y is N-L-R$^1$ and L is a —(CR$^a$R$^b$)—. In a specific aspect of these embodiments of Formulas (II) and (IIa), L is —CR$^a$R$^b$— (e.g., m is 1). In a more specific aspect of these embodiments of Formulas (II) and (IIa), L is —CH$_2$— (e.g., R$^a$ and R$^b$ are hydrogen). In another specific aspect of these embodiments of Formulas (II) and (IIa), R$^1$ is C$_{1-4}$ alkyl substituted with 0-3 occurrences of R$^g$. In a more specific aspect of these embodiments of Formulas (II) and (IIa), R$^1$ is C$_{1-4}$ alkyl substituted with 0 occurrences of R$^g$ (e.g., methyl). In another specific aspect of these embodiments of Formulas (II) and (IIa), R$^1$ is aryl substituted with 0-3 occurrences of R$^f$. In a more specific aspect of these embodiments of Formulas (II) and (IIa), R$^1$ is aryl substituted with 0 occurrences of R$^f$. In an even more specific aspect of these embodiments of Formulas (II) and (IIa), R$^1$ is unsubstituted phenyl.

In certain embodiments of Formulas (II) and (IIa), X is N-L-R$^1$.

In certain embodiments of Formulas (II) and (IIa), X is N-L-R$^1$, and L is a bond. In one aspect of these embodiments of Formulas (II) and (IIa), R$^1$ is hydrogen. In still another aspect of these embodiments of Formulas (II) and (IIa), R$^1$ is C$_{1-4}$ alkyl substituted with 0-3 occurrences of R$^g$. In a more specific aspect of these embodiments of Formulas (II) and (IIa), R$^1$ is C$_{1-4}$ alkyl substituted with 0 occurrences of R$^g$ (e.g., methyl).

In some embodiments of Formulas (II) and (IIa), X is N-L-R$^1$, and L is —(CR$^a$R$^b$)$_m$—. In a specific aspect of these embodiments of Formulas (II) and (IIa), L is —CR$^a$R$^b$— (e.g., m is 1). In an even more specific aspect of these embodiments of Formulas (II) and (IIa), L is —CH$_2$— (e.g, R$^a$ and R$^b$ are hydrogen). In another specific aspect of these embodiments of Formulas (II) and (IIa), R$^1$ is aryl substituted with 0-3 occurrences of R$^f$. In a more specific aspect of these embodiments of Formulas (II) and (IIa), R$^1$ is unsubstituted phenyl.

In some embodiments of Formulas (II) and (IIa), Y is O.

In some embodiments of Formulas (II) and (IIa), Y is O and X is N-L-R$^1$.

In certain embodiments of Formulas (II) and (IIa), X is N-L-R$^1$, Y is O and L is a bond. In one aspect of these embodiments of Formulas (II) and (IIa), R$^1$ is hydrogen. In still another aspect of these embodiments of Formulas (II) and (IIa), R$^1$ is C$_{1-4}$ alkyl substituted with 0-3 occurrences of R$^g$. In a more specific aspect of these embodiments of Formulas (II) and (IIa), R$^1$ is C$_{1-4}$ alkyl substituted with 0 occurrences of R$^g$ (e.g., methyl).

In some embodiments of Formulas (II) and (IIa), X is N-L-R$^1$, Y is O and L is —(CR$^a$R$^b$)$_m$—. In a specific aspect of these embodiments of Formulas (II) and (IIa), L is —CR$^a$R$^b$— (e.g., m is 1). In an even more specific aspect of these embodiments of Formulas (II) and (IIa), L is —CH$_2$— (e.g, R$^a$ and R$^b$ are hydrogen). In another specific aspect of these embodiments of Formulas (II) and (IIa), R$^1$ is aryl substituted with 0-3 occurrences of R$^f$. In a more specific aspect of these embodiments of Formulas (II) and (IIa), R$^1$ is unsubstituted phenyl.

In certain embodiments of Formulas (II) and (IIa), n is 0.

In certain embodiments of Formulas (II) and (IIa), A is aryl (e.g., monocyclic or bicyclic aryl) substituted with 0-3 occurrences of R$^d$. In some embodiments of Formulas (II) and (IIa), A is 5-8 membered monocyclic aryl (e.g., phenyl) substituted with 0-3 occurrences of R$^d$. In some embodiments of Formulas (II) and (IIa), A is phenyl substituted with 0-3 occurrences of R$^d$.

In some embodiments of Formulas (II) and (IIa), A is phenyl substituted with 2 occurrences of R$^d$. In certain embodiments of Formulas (II) and (IIa), both R$^d$ are halo (e.g., 3-chloro-4-fluorophenyl). In some embodiments of Formulas (II) and (IIa), one R$^d$ is alkyl and one R$^d$ is halo (e.g., 3-methyl-4-fluorophenyl).

In another aspect, the present invention is directed to a compound of formula (III),

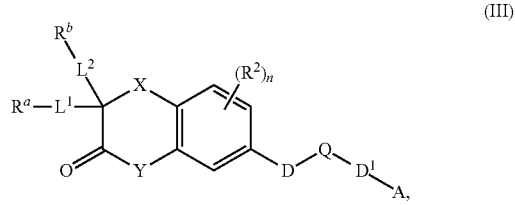

(III)

wherein

X and Y are each independently selected from O and N—R$^1$;

Q is C(O), SO$_2$, or —(CH$_2$)$_h$—;

L$^1$ and L$^2$ are each independently selected from a bond, —O—, C(O)—, —C(O)O—, —OC(O)—, —C(O)NR$^c$—, —NR$^c$C(O)—, —S—, —SO— and —SO$_2$—;

D and D$^1$ are each independently selected from a bond, O and NR$^c$, provided that D and D$^1$ are not both a bond;

A is aryl or heteroaryl, each of which is substituted with 0-3 occurrences of R$^f$;

each R$^1$ is independently selected from hydrogen or C$_{1-4}$ alkyl, wherein each C$_{1-4}$ alkyl is substituted with 0-3 occurrences of R$^f$;

R$^a$ and R$^b$ are each independently selected from hydrogen, C$_{1-4}$ alkyl, haloC$_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of R$^f$ and each alkyl and haloalkyl is substituted with 0-3 occurrences of R$^g$; or one of R$^a$ or R$^b$ is taken together with R$^1$ and the atoms to which they are respectively attached to form an optionally substituted five-membered heterocylyl;

each R$^c$ is independently selected from hydrogen and C$_{1-4}$ alkyl;

each R$^d$ is independently selected from halo, halo C$_{1-4}$ alkyl, C$_{1-4}$ alkyl, nitro, —NR$^c$R$^c$, —NHCH(NR$^c$R$^c$)NR$^c$R$^c$, —NHC(=NR$^c$R$^c$)NR$^c$R$^c$, —C(O)NR$^c$R$^c$, cyano, —SR$^c$ and —OR$^c$, or two R$^d$, attached to the same or adjacent carbon atoms, taken together with the atoms to which they are attached form an optionally substituted heterocyclyl;

each R$^f$ is independently selected from halo, halo C$_{1-4}$ alkyl, C$_{1-4}$ alkyl, nitro, cyano, —OH and —O(C$_{1-4}$ alkyl), or two R$^f$, attached to the same or adjacent carbon atoms, taken together with the atoms to which they are attached form an optionally substituted heterocyclyl;

each R$^g$ is independently selected from nitro, cyano, —OH, —O(C$_{1-4}$ alkyl) or two R$^g$, attached to the same or adjacent carbon atoms, taken together with the atoms to which they are attached form an optionally substituted heterocyclyl;

each R$^2$ is independently selected from halo, halo C$_{1-4}$ alkyl, C$_{1-4}$ alkyl, C$_{1-4}$ alkoxy and hydroxyl;

h is 1, 2 or 3; and n is 0, 1, 2 or 3; provided that

1) D-Q-D$^1$-A is not —SO$_3$-phenyl or —SO$_3$-p-methylphenyl;

2) when Y is NR$^c$, then Q is not C(O);

3) when Y is NH, D-Q-D$^1$- is not SO$_2$NR$^c$ or NR$^c$SO$_2$; and 4) the compound is not:
i) N-(3-fluoro-2-methylphenyl)-3,4-dihydro-4-methyl-3-oxo-2H-1,4-benzoxazine-6-sulfonamide;
ii) methyl 4,5-dimethoxy-2-(4-methyl-3-oxo-3,4-dihydro-2H-benzo[b][1,4]oxazine-6-sulfonamido)-phenethylcarbamate;
iii) 1-(difluoromethyl)-N-(3,4-dihydro-4-methyl-3-oxo-2H-1,4-benzoxazin-6-yl)-5-methyl-1H-pyrazole-4-sulfonamide;
iv) N-(3,4-dihydro-4-methyl-3-oxo-2H-1,4-benzoxazin-6-yl)-4-fluoro-3-methyl-benzenesulfonamide;
v) 7-chloro-N-(3,4-dihydro-4-methyl-3-oxo-2H-1,4-benzoxazin-6-yl)-2,3-dihydro-1,4-benzodioxin-6-sulfonamide;
vi) N-(3,4-dihydro-4-methyl-3-oxo-2H-1,4-benzoxazin-6-yl)-1,5-dimethyl-1H-pyrazole-4-sulfonamide;
vii) N-(3,4-dihydro-4-methyl-3-oxo-2H-1,4-benzoxazin-6-yl)-2-fluoro-5-methyl-benzenesulfonamide; or
viii) 5-chloro-N-(3,4-dihydro-4-methyl-3-oxo-2H-1,4-benzoxazin-6-yl)-2,4-dimethoxy-benzenesulfonamide In certain embodiments of Formula (III), D is a bond.

In some embodiments of Formula (III), D is oxygen.

In some embodiments of Formula (III), D is NR$^c$. In one aspect of these embodiments of Formula (III), D is NH. In another aspect of these embodiments of Formula (III), D is N(C$_{1-4}$ alkyl). In a more specific aspect of these embodiments of Formula (III), D is N(CH$_3$).

In certain embodiments of Formula (III), D$^1$ is O.

In certain embodiments of Formula (III), D$^1$ is NR$^c$. In one aspect of these embodiments of Formula (III), D$^1$ is NH. In a more specific aspect of these embodiments of Formula (III), D$^1$ is N(C$_{1-4}$ alkyl). In a more specific aspect of these embodiments of Formula (III), D$^1$ is N(CH$_3$).

In certain embodiments of Formula (III), Q is SO$_2$.

In some embodiments of Formula (III), Q is (CH$_2$)$_h$. In one aspect of these embodiments of Formula (III), h is 1 (i.e., Q is CH$_2$).

In some embodiments of Formula (III), Q is C(O).

In certain embodiments of Formula (III), D is a bond, D$^1$ is NR$^c$ and Q is SO$_2$. In one aspect of these embodiments of Formula (III), D$^1$ is NH. In another aspect of these embodiments of Formula (III), D$^1$ is N(C$_{1-4}$ alkyl). In a more specific aspect of these embodiments of Formula (III), D$^1$ is N(CH$_3$).

In certain embodiments of Formula (III), D is a bond, D$^1$ is NR$^c$ and Q is C(O). In one aspect of these embodiments of Formula (III), D$^1$ is NH. In another aspect of these embodiments of Formula (III), D$^1$ is (C$_{1-4}$ alkyl). In a more specific aspect of these embodiments of Formula (III), D$^1$ is N(CH$_3$).

In certain embodiments of Formula (III), D is a bond, D$^1$ is NR$^c$ and Q is (CH$_2$)$_h$. In one aspect of these embodiments of Formula (III), h is 1. In one aspect of these embodiments of Formula (III), D$^1$ is NH. In another aspect of these embodiments of Formula (III), D$^1$ is N(C$_{1-4}$ alkyl). In a more specific aspect of these embodiments of Formula (III), D$^1$ is N(CH$_3$).

In certain embodiments of Formula (III), D is oxygen, Q is C(O) and D$^1$ is NR$^c$. In one aspect of these embodiments of Formula (III), D$^1$ is NH.

In certain embodiments of Formula (III), D is NR$^c$, Q is C(O) and D$^1$ is oxygen. In one aspect of these embodiments of Formula (III), D is NH. In another aspect of these embodiments of Formula (III), D is N(C$_{1-4}$ alkyl). In a more specific aspect of these embodiments of Formula (III), D is N(CH$_3$).

In certain embodiments of Formula (III), D is a bond, Q is C(O) and D$^1$ is oxygen.

In another embodiment, the present invention is directed to a compound of formula (III), wherein D is a bond, Q is S(O)$_2$ and D$^1$ is —NH—, the compound having the formula (IIIa):

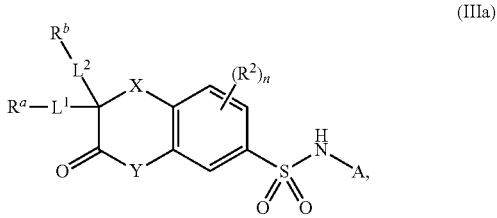

(IIIa)

wherein X, Y, R$^a$, R$^b$, R$^c$, R$^d$, R$^f$, R$^g$, L$^1$, L$^2$, R$^1$, R$^2$, A and n are as described above.

The following embodiments and aspects thereof relate to both Formula (III) and Formula (IIIa).

In certain embodiments of Formulas (III) and (IIIa), X is O. In one aspect of these embodiments of Formulas (III) and (IIIa), Y is N—$R^1$. In a more specific aspect of these embodiments of Formulas (III) and (IIIa), Y is NH. In another aspect of these embodiments of Formulas (III) and (IIIa), Y is N($C_{1-4}$ alkyl), wherein the $C_{1-4}$ alkyl is substituted with 0-3 occurrences of $R^f$. In a more specific aspect of these embodiments of Formulas (III) and (IIIa), Y is N($C_{1-4}$ alkyl), wherein the alkyl is substituted with 0 occurrences of $R^f$. In an even more specific aspect of these embodiments of Formulas (III) and (IIIa), Y is N($CH_3$).

In some embodiments of Formulas (III) and (IIIa), X is N—$R^1$. In one aspect of these embodiments of Formulas (III) and (IIIa), $R^1$ is hydrogen.

In some embodiments of Formulas (III) and (IIIa), Y is N—$R^1$. In one aspect of these embodiments of Formulas (III) and (IIIa), $R^1$ is hydrogen.

In certain embodiments of Formulas (III) and (IIIa), Y is O. In one aspect of these embodiments of Formulas (III) and (IIIa), X is N—$R^1$. In a more specific aspect of these embodiments of Formulas (III) and (IIIa), X is NH. In another aspect of these embodiments of Formulas (III) and (IIIa), X is N($C_{1-4}$ alkyl), wherein the $C_{1-4}$ alkyl is substituted with 0-3 occurrences of $R^f$. In a more specific aspect of these embodiments of Formulas (III) and (IIIa), X is N($C_{1-4}$ alkyl) wherein the alkyl is substituted with 0 occurrences of $R^f$. In a more specific aspect of these embodiments of Formulas (III) and (IIIa), X is N($CH_3$).

In certain embodiments of Formulas (III) and (IIIa), n is 0.
In certain embodiments of Formulas (III) and (IIIa), n is 1.
In certain embodiments of Formulas (III) and (IIIa), $R^a$ is hydrogen.

In some embodiments of Formulas (III) and (IIIa), $R^b$ is hydrogen.

In certain embodiments of Formulas (III) and (IIIa), $L^1$ is a bond. In one aspect of this embodiment of Formulas (III) and (IIIa), $R^a$ is hydrogen.

In some embodiments of Formulas (III) and (IIIa), $L^2$ is a bond. In one aspect of this embodiment of Formulas (III) and (IIIa), $R^b$ is hydrogen.

In certain embodiments of Formulas (III) and (IIIa), A is aryl (e.g., monocyclic or bicyclic aryl) substituted with 0-3 occurrences of $R^d$. In one aspect of these embodiments of Formulas (III) and (IIIa), A is 5-8 membered monocyclic aryl (e.g., phenyl) substituted with 0-3 occurrences of $R^d$. In a more specific aspect of these embodiments of Formulas (III) and (IIIa), A is phenyl substituted with 0-3 occurrences of $R^d$. In an even more specific aspect of these embodiments of Formulas (III) and (IIIa), A is phenyl substituted with 0 occurrences of $R^d$.

In certain specific embodiments of Formulas (III) and (IIIa), A is phenyl substituted with 1 occurrence of $R^d$. In one aspect of these embodiments of Formulas (III) and (IIIa), $R^d$ is halo (e.g., p-fluorophenyl or m-chlorophenyl). In some embodiments of Formulas (III) and (IIIa), $R^d$ is alkyl (e.g., methyl). In another aspect of these embodiments of Formulas (III) and (IIIa), $R^d$ is —$OR^c$ (e.g., p-substituted —$OR^c$). In a more specific aspect of these embodiments of Formulas (III) and (IIIa), $R^d$ is p-substituted —$OR^c$. In another more specific aspect of these embodiments of Formulas (III) and (IIIa), $R^d$ is —O-alkyl (e.g., —O-methyl).

In certain embodiments of Formulas (III) and (IIIa), A is phenyl substituted with 2 occurrences of $R^d$. In one aspect of these embodiments of Formulas (III) and (IIIa), both $R^d$ are halo (e.g., 3-chloro-4-fluorophenyl). In another aspect of these embodiments of Formulas (III) and (IIIa), both $R^d$ are alkyl (e.g., 3,5-dimethylphenyl). In another aspect of these embodiments of Formulas (III) and (IIIa), one $R^d$ is alkyl and one $R^d$ is halo (e.g., 3-methyl-4-fluorophenyl). In yet another aspect of these embodiments of Formulas (III) and (IIIa), two $R^d$, attached to the same or adjacent carbon atoms, taken together with the atoms to which they are attached form an optionally substituted heterocyclyl. In a more specific aspect of these embodiments of Formulas (III) and (IIIa), each $R^d$ is —$OR^c$ and the two —$OR^c$ taken together with the carbon atoms to which they are attached form an optionally substituted heterocyclyl. In another more specific aspect of these embodiments of Formulas (III) and (IIIa), two —$OR^c$ form 3,4-ethylenedioxy. In another even more specific aspect of these embodiments of Formulas (III) and (IIIa), two —$OR^c$ form 3,4-methylenedioxy.

In another aspect, the present invention is directed to a compound of formula (IV),

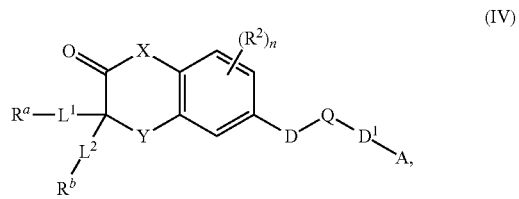

(IV)

wherein
X and Y are each independently selected from O and N—$R^1$;
Q is C(O), $SO_2$, or —$(CH_2)_h$—;
$L^1$ and $L^2$ are each independently selected from a bond, —O—, C(O)—, —C(O)O—, —OC(O)—, —C(O)$NR^c$—, —$NR^cC(O)$—, —S—, —SO— and —$SO_2$—;
D and $D^1$ are each independently selected from a bond, O and $NR^c$, provided that D and $D^1$ are not both a bond;
A is aryl or heteroaryl, each of which is substituted with 0-3 occurrences of $R^d$;
each $R^1$ is independently selected from hydrogen or $C_{1-4}$ alkyl; wherein each $C_{1-4}$ alkyl is substituted with 0-3 occurrences of $R^f$;
$R^a$ and $R^b$ are each independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocycloalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$; or
one of $R^a$ or $R^b$ is taken together with a Y—$R^1$ or X—$R^1$ and the atoms to which they are respectively attached to form an optionally substituted five-membered heterocyclyl;
each $R^c$ is independently selected from hydrogen and $C_{1-4}$ alkyl;
each $R^d$ is independently selected from halo, halo $C_{1-4}$ alkyl, $C_{1-4}$ alkyl, nitro, —$NR^cR^c$, —NHCH($NR^cR^c$)$NR^cR^c$, —NHC(=$NR^cR^c$)$NR^cR^c$, —C(O)$NR^cR^c$, cyano, —$SR^c$ and —$OR^c$, or two $R^d$, attached to the same or adjacent carbon atoms, taken together with the atoms to which they are attached form an optionally substituted heterocyclyl;
each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;
each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl;

h is 1, 2 or 3; and n is 0, 1, 2 or 3; provided that:

1) D-Q-$D^1$-A is not O-benzyl;
2) when Y is O, X is not N—$R^1$; and
3) the compound of formula (IV) is not:
(E)-N-(3,3-dimethyl-2-oxo-3,4-dihydro-2H-benzo[b][1,4]oxazin-6-yl)-4-(3,3,3-trifluoroprop-1-en-1-yl)benzamide;
(E)-N-(3,3-dimethyl-2-oxo-3,4-dihydro-2H-benzo[b][1,4]oxazin-6-yl)-N-methyl-4-(3,3,3-trifluoroprop-1-en-1-yl)benzamide;
3-[2-(4-bromophenyl)-2-oxoethyl]-3,4-dihydro-6-methyl-2H-1,4-benzoxazin-2-one; or
4-[[(3,4-dihydro-2-oxo-2H-1,4-benzoxazin-6-yl)amino]sulfonyl]-5-methyl-2-furancarboxylic acid ethyl ester.

In certain embodiments of Formula (IV), D is a bond.
In some embodiments of Formula (IV), D is oxygen.
In some embodiments of Formula (IV), D is $NR^c$. In one aspect of these embodiments of Formula (IV), D is NH. In another aspect of these embodiments of Formula (IV), D is $N(C_{1-4}$ alkyl). In a more specific aspect of these embodiments of Formula (IV), D is $N(CH_3)$.

In certain embodiments of Formula (IV), $D^1$ is O.
In certain embodiments of Formula (IV), $D^1$ is $NR^c$. In one aspect of these embodiments of Formula (IV), $D^1$ is NH. In a more specific aspect of these embodiments of Formula (IV), $D^1$ is $N(C_{1-4}$ alkyl). In a more specific aspect of these embodiments of Formula (IV), $D^1$ is $N(CH_3)$.

In certain embodiments of Formula (IV), Q is $SO_2$.
In some embodiments of Formula (IV), Q is $(CH_2)_h$. In one aspect of these embodiments of Formula (IV), h is 1 (i.e., Q is $CH_2$).

In some embodiments of Formula (IV), Q is C(O).
In certain embodiments of Formula (IV), D is a bond, $D^1$ is $NR^c$ and Q is $SO_2$. In one aspect of these embodiments of Formula (IV), $D^1$ is NH. In another aspect of these embodiments of Formula (IV), $D^1$ is $N(C_{1-4}$ alkyl). In a more specific aspect of these embodiments of Formula (IV), $D^1$ is $N(CH_3)$.

In certain embodiments of Formula (IV), D is a bond, $D^1$ is $NR^c$ and Q is C(O). In one aspect of these embodiments of Formula (IV), $D^1$ is NH. In another aspect of these embodiments of Formula (IV), $D^1$ is ($C_{1-4}$ alkyl). In a more specific aspect of these embodiments of Formula (IV), $D^1$ is $N(CH_3)$.

In certain embodiments of Formula (IV), D is a bond, $D^1$ is $NR^c$ and Q is $(CH_2)_h$. In one aspect of these embodiments of Formula (IV), h is 1. In another aspect of these embodiments of Formula (IV), $D^1$ is NH. In another aspect of these embodiments of Formula (IV), $D^1$ is $N(C_{1-4}$ alkyl). In a more specific aspect of these embodiments of Formula (IV), $D^1$ is $N(CH_3)$.

In certain embodiments of Formula (IV), D is oxygen, Q is C(O) and $D^1$ is $NR^c$. In one aspect of these embodiments of Formula (IV), $D^1$ is NH.

In certain embodiments of Formula (IV), D is $NR^c$, Q is C(O) and $D^1$ is oxygen. In one aspect of these embodiments of Formula (IV), D is NH. In another aspect of these embodiments of Formula (IV), D is $N(C_{1-4}$ alkyl). In a more specific aspect of these embodiments of Formula (IV), D is $N(CH_3)$.

In certain embodiments of Formula (IV), D is a bond, Q is C(O) and $D^1$ is oxygen.

In another aspect, the present invention is directed to a compound of formula (IV), wherein D is a bond, Q is $S(O)_2$ and $D^1$ is —NH—, the compound having the formula (IVa):

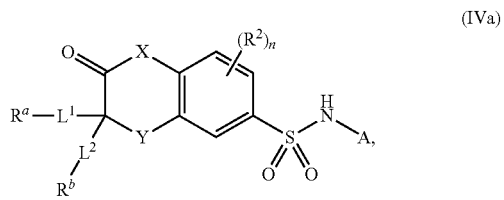

(IVa)

wherein X, Y, $R^a$, $R^b$, $R^c$, $R^d$, $R^f$, $R^g$, $L^1$, $L^2$, $R^1$, $R^2$, A and n are as described above.

The following embodiments and aspects thereof relate to both Formula (IV) and Formula (IVa).

In certain embodiments of Formulas (IV) and (IVa), X is O. In one aspect of these embodiments of Formulas (IV) and (IVa), Y is N—$R^1$. In a more specific aspect of these embodiments of Formulas (IV) and (IVa), Y is NH. In another aspect of these embodiments of Formulas (IV) and (IVa), Y is $N(C_{1-4}$ alkyl), wherein the $C_{1-4}$ alkyl is substituted with 0-3 occurrences of $R^f$. In a more specific aspect of these embodiments of Formulas (IV) and (IVa), Y is $N(C_{1-4}$ alkyl, wherein the alkyl is substituted with 0 occurrences of $R^f$. In an even more specific aspect of these embodiments of Formulas (IV) and (IVa), Y is $N(CH_3)$.

In some embodiments of Formulas (IV) and (IVa), X is N—$R^1$. In one aspect of these embodiments of Formulas (IV) and (IVa), $R^1$ is hydrogen.

In some embodiments of Formulas (IV) and (IVa), Y is N—$R^1$. In one aspect of these embodiments of Formulas (IV) and (IVa), $R^1$ is hydrogen.

In certain embodiments of Formulas (IV) and (IVa), Y is O. In one aspect of these embodiments of Formulas (IV) and (IVa), X is N—$R^1$. In a more specific aspect of these embodiments of Formulas (IV) and (IVa), X is NH. In another aspect of these embodiments of Formulas (IV) and (IVa), X is $N(C_{1-4}$ alkyl), wherein the $C_{1-4}$ alkyl is substituted with 0-3 occurrences of $R^f$. In a more specific aspect of these embodiments of Formulas (IV) and (IVa), X is $N(C_{1-4}$ alkyl) wherein the alkyl is substituted with 0 occurrences of $R^f$. In a more specific aspect of these embodiments of Formulas (IV) and (IVa), X is $N(CH_3)$.

In certain embodiments of Formulas (IV) and (IVa), n is 0.
In certain embodiments of Formulas (IV) and (IVa), n is 1.
In certain embodiments of Formulas (IV) and (IVa), $R^a$ is hydrogen.
In some embodiments of Formulas (IV) and (IVa), $R^b$ is hydrogen.
In certain embodiments of Formulas (IV) and (IVa), $L^1$ is a bond. In one aspect of this embodiment of Formulas (IV) and (IVa), $R^a$ is hydrogen.
In some embodiments of Formulas (IV) and (IVa), $L^2$ is a bond. In one aspect of this embodiment of Formulas (IV) and (IVa), $R^b$ is hydrogen.

In certain embodiments of Formulas (IV) and (IVa), A is aryl (e.g., monocyclic or bicyclic aryl) substituted with 0-3 occurrences of $R^d$. In one aspect of these embodiments of Formulas (IV) and (IVa), A is 5-8 membered monocyclic aryl (e.g., phenyl) substituted with 0-3 occurrences of $R^d$. In a more specific aspect of these embodiments of Formulas (IV) and (IVa), A is phenyl substituted with 0-3 occurrences of $R^d$. In an even more specific aspect of these embodiments of Formulas (IV) and (IVa), A is phenyl substituted with 0 occurrences of $R^d$.

In certain specific embodiments of Formulas (IV) and (IVa), A is phenyl substituted with 1 occurrence of $R^d$. In one aspect of these embodiments of Formulas (IV) and (IVa), $R^d$ is halo (e.g., p-fluorophenyl or m-chlorophenyl). In some embodiments of Formulas (IV) and (IVa), $R^d$ is alkyl (e.g., methyl). In another aspect of these embodiments of Formulas (IV) and (IVa), $R^d$ is —$OR^c$ (e.g., p-substituted —$OR^c$). In a more specific aspect of these embodiments of Formulas (IV) and (IVa), $R^d$ is p-substituted —$OR^c$. In another more specific aspect of these embodiments of Formulas (IV) and (IVa), $R^d$ is —O-alkyl (e.g., —O-methyl).

In certain embodiments of Formulas (IV) and (IVa), A is phenyl substituted with 2 occurrences of $R^d$. In one aspect of these embodiments of Formulas (IV) and (IVa), both $R^d$ are halo (e.g., 3-chloro-4-fluorophenyl). In another aspect of these embodiments of Formulas (IV) and (IVa), both $R^d$ are alkyl (e.g., 3,5-dimethylphenyl). In another aspect of these embodiments of Formulas (IV) and (IVa), one $R^d$ is alkyl and one $R^d$ is halo (e.g., 3-methyl-4-fluorophenyl). In yet another aspect of these embodiments of Formulas (IV) and (IVa), two $R^d$, attached to the same or adjacent carbon atoms, taken together with the carbon atoms to which they are attached form an optionally substituted heterocyclyl. In a more specific aspect of these embodiments of Formulas (IV) and (IVa), each $R^d$ is —$OR^c$ and the two —$OR^c$ taken together with the carbon atoms to which they are attached form an optionally substituted heterocyclyl. In another more specific aspect of these embodiments of Formulas (IV) and (IVa), two —$OR^c$ form 3,4-ethylenedioxy. In another even more specific aspect of these embodiments of Formulas (IV) and (IVa), two —$OR^c$ form 3,4-methylenedioxy.

In another embodiment, the present invention is directed to a pharmaceutically acceptable salt of a compound of formulas (I), (II), (III) or (IV). In another aspect, the present invention is directed to a pharmaceutically acceptable salt of a compound of formulas (Ia), (IIa), (IIIa) or (IVa).

In another embodiment, the present invention is directed to a composition (e.g., a pharmaceutical composition) comprising a compound of formulas (I), (II), (III) or (IV). In some embodiments, the composition further comprises a pharmaceutically acceptable carrier. In another aspect, the present invention is directed to a composition (e.g., a pharmaceutical composition) comprising a compound of formulas (Ia), (IIa), (IIIa) or (IVa).

In one embodiment, the invention features a method of modulating (e.g., increasing) the level of PKM2 activity and/or glycolysis (e.g., modulating the endogenous ability of a cell in the patient to down regulate PKM2) in a patient in need thereof. The method comprises the step of administering an effective amount of a compound described herein to the patient in need thereof, thereby modulating (e.g., increasing) the level of PKM2 activity and/or glycolysis in the patient. In some embodiments, a compound of the invention an activator is used to maintain PKM2 in its active conformation or activate pyruvate kinase activity in proliferating cells as a means to divert glucose metabolites into catabolic rather than anabolic processes in the patient.

In another embodiment, the invention features a method of inhibiting cell proliferation in a patient in need thereof. The method comprises the step of administering an effective amount of a compound described herein to the patient in need thereof, thereby inhibiting cell proliferation in the patient. E.g., this method can inhibit growth of a transformed cell, e.g., a cancer cell, or generally inhibit growth in a PKM2-dependent cell that undergoes aerobic glycolysis.

In another embodiment, the invention features a method of treating a patient suffering from or susceptible to a disease or disorder associated with the function of PKM2 in a patient in need thereof. The method comprises the step of administering an effective amount of a compound described herein to the patient in need thereof, thereby treating, preventing or ameliorating the disease or disorder in the patient. In another embodiment the compound of the invention is provided in a pharmaceutical composition.

In another embodiment, the method includes a first step of identifying or selecting a patient who would benefit from modulation (e.g., activation) of PKM2 by determining the level of PKM2 activity in a patient or more particularly in an organ or cell of the patient (e.g., as opposed to merely being in need of treatment of the disorder itself, e.g., cancer). The level of PKM2 would be compared to a control (e.g., the PKM2 activity of another patient not suffering from the disorder (e.g., cancer) or the PKM2 activity of the same patient taken at an earlier time) to determine if the current level of PKM2 activity warranted treatment with a compound of this invention. In one aspect, a patient who has a level of PKM2 activity below that of a control would be a candidate for treatment with a compound of this invention.

In another embodiment, the method includes the subsequent step of monitoring the level of PKM2 activity in a patient or more particularly in an organ or cell of the patient during the course of or following treatment with a compound of this invention to determine the efficacy of the treatment. The level of PKM2 would be compared to a control (e.g., PKM2 activity of the same patient taken just prior to treatment) to determine if the PKM2 activity had been altered by the treatment, thus providing evidence of the efficacy of the treatment. In one aspect, an increase in PKM2 activity during the course of or following treatment is indicative that the treatment was effective.

In another embodiment, the selected patient is a patient suffering from or susceptible to a disorder or disease identified herein, e.g., a disorder characterized by unwanted cell growth or proliferation, e.g., cancer, obesity, diabetes, atherosclerosis, restenosis, and autoimmune diseases.

In another embodiment, the compound described herein is administered at a dosage and frequency sufficient to increase lactate production or oxidative phosphorylation.

DEFINITIONS

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, and —$CH_2CH_2CH_2$—.

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkynyl" refers to a monovalent straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH (alkyl) and —NH(alkyl)$_2$ radicals respectively. The term "aralkylamino" refers to a —NH(aralkyl) radical. The term alkylaminoalkyl refers to a (alkyl)NH-alkyl- radical; the term dialkylaminoalkyl refers to a (alkyl)$_2$N-alkyl- radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively). Any ring atom can be substituted (e.g., by one or more substituents).

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition.

The term "heterocyclylalkyl", as used herein, refers to an alkyl group substituted with a heterocyclyl group.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The terms "hetaralkyl" and "heteroaralkyl", as used herein, refers to an alkyl group substituted with a heteroaryl group.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group that replaces a hydrogen atom on an alkyl, cycloalkyl, alkenyl, alkynyl, heterocyclyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as CF$_3$), aryl, heteroaryl, aralkyl, heteroaralkyl, heterocyclyl, alkenyl, alkynyl, cycloalkenyl, alkoxy, haloalkoxy (e.g., perfluoroalkoxy such as OCF$_3$), halo, hydroxy, carboxy, carboxylate, cyano, nitro, amino, alkyl amino, SO$_3$H, sulfate, phosphate, methylenedioxy (—O—CH$_2$—O— wherein oxygens are attached to vicinal atoms), ethylenedioxy, oxo, thioxo (e.g., C=S), imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "selective" is meant at least 2-fold, 3-fold, 4-fold, 5-fold, 6-fold, or 10-fold greater modulation (e.g., activation) of M2 than M1.

The term "activator" as used herein means an agent that (measurably) increases the activity of a pyruvate kinase (e.g., PKM2) or causes pyruvate kinase (e.g., PKM2) activity to increase to a level that is greater than PKM2's basal levels of activity. For example, the activator may mimic the effect caused by a natural ligand (e.g., FBP). The activator effect caused by the agent may be to the same, or to a greater, or to a lesser extent than the activating effect caused by a natural ligand, but the same type of effect is caused. Peptides, nucleic acids, and small molecules may be activators. An agent can be evaluated to determine if it is an activator by measuring either directly or indirectly the activity of the pyruvate kinase when subjected to the agent. The activity of the agent can be measured, for example, against a control substance. In some instances, the activity measured of the agent is for activation of PKM2. The activity of PKM2 can be measured, for example, by monitoring the concentration of a substrate such as ATP or NADH.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that modulate PKM2, for example, activate PKM2. Compounds that modulate PKM2, e.g., activate PKM2, can be used to treat disorders such as neoplastic disorders (e.g., cancer) or fat related disorders (e.g., obesity). Compounds include those of Formula I described herein. In some embodiments, a compound described herein modulates PKM2 by interacting (e.g., binding) with the FBP binding pocket. For example, a compound described herein can compete with FBP binding in PKM2.

A compound described herein may be an activator of PKM2. For simplicity, the activation activity of these compounds is represented as an $AC_{50}$ in the Tables below and throughout the application. Exemplary compounds are shown in Tables 1-4. As shown in Tables 1-4, A refers to an activator of PKM2 with an $AC_{50}$<100 nM. B refers to an activator of PKM2 with an $AC_{50}$ between 100 nM and 500 nM. C refers to an activator of PKM2 with an $AC_{50}$ greater than 500 nM.

TABLE 1

| Compound | $AC_{50}$ |
|---|---|
| (structure) | A |
| (structure) | A |

TABLE 2

| Compound | $AC_{50}$ |
|---|---|
| (structure) | B |
| (structure) | B |
| (structure) | B |
| (structure) | B |
| (structure) | C |

TABLE 3

| Compound | $AC_{50}$ |
|---|---|
| (structure) | C |
| (structure) | C |

TABLE 3-continued

| Compound | AC$_{50}$ |
|---|---|
| (benzoxazinone sulfonamide with benzodioxine) | C |
| (benzoxazinone sulfonamide with 4-methoxyphenyl) | C |
| (N-methyl benzoxazinone sulfonamide with benzodioxine) | C |
| (N-methyl benzoxazinone sulfonamide with 3,5-dimethylphenyl) | A |
| (N-methyl benzoxazinone sulfonamide with 4-fluorophenyl) | C |
| (N-methyl benzoxazinone sulfonamide with 4-methoxyphenyl) | C |
| (N-methyl benzoxazinone sulfonamide with 4-fluoro-3-methylphenyl) | A |
| (N-methyl benzoxazinone sulfonamide with 3-chloro-4-fluorophenyl) | A |

TABLE 3-continued

| Compound | AC$_{50}$ |
|---|---|
| (N-methyl benzoxazinone sulfonamide with 3-chlorophenyl) | A |
| (N-methyl benzoxazinone sulfonamide with benzodioxole) | A |

TABLE 4

| Compound | AC$_{50}$ |
|---|---|
| (N-methyl benzoxazinone isomer sulfonamide with 3-chlorophenyl) | A |
| (N-methyl benzoxazinone isomer sulfonamide with 4-fluoro-3-methylphenyl) | A |
| (N-methyl benzoxazinone isomer sulfonamide with 3-chloro-4-fluorophenyl) | A |

The compounds described herein can be made using a variety of synthetic techniques.

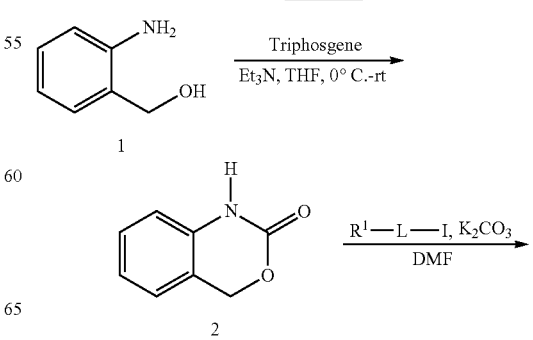

Scheme 1.

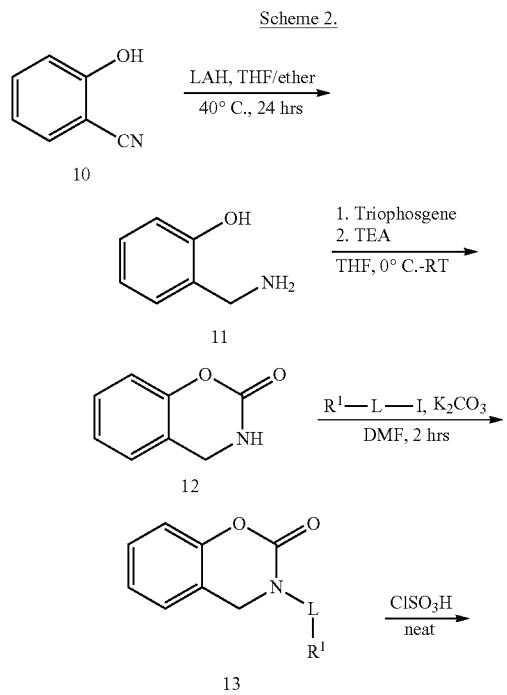

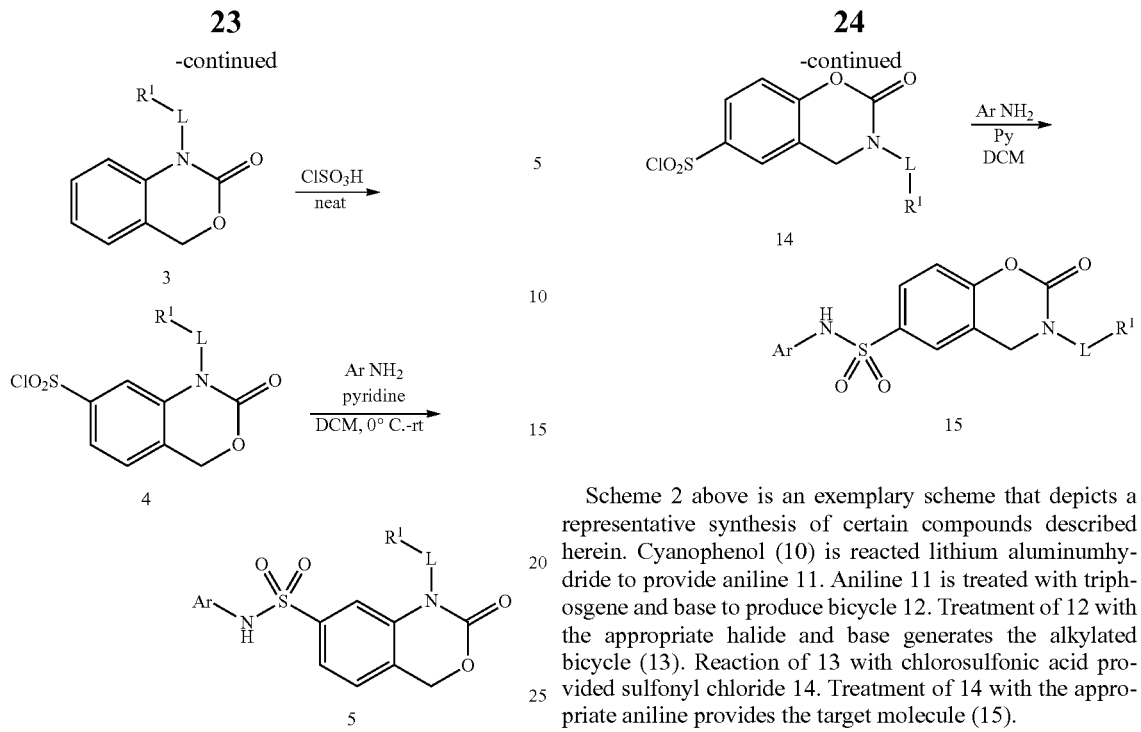

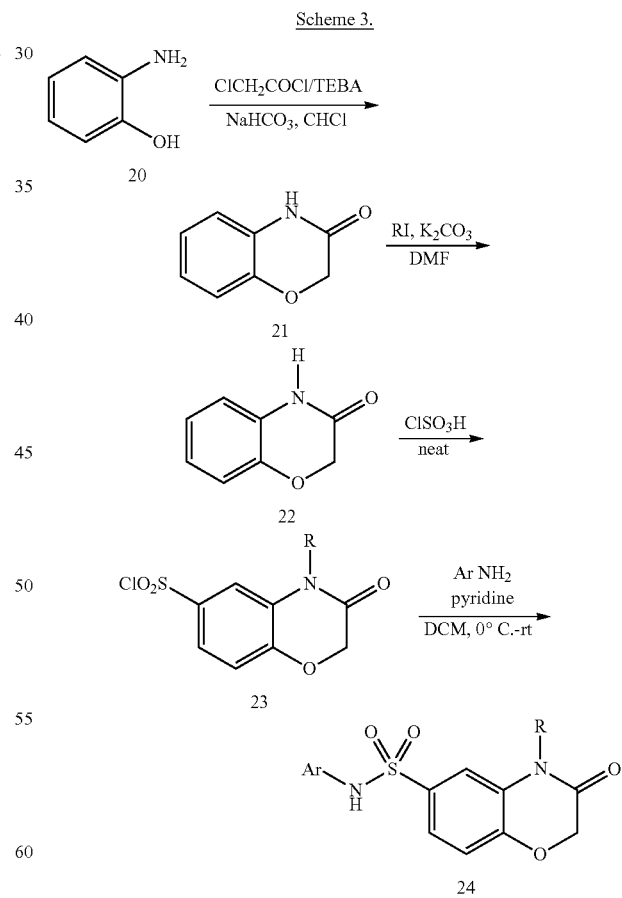

Scheme 1 above is an exemplary scheme that depicts a representative synthesis of certain compounds described herein. Aniline 1 is reacted with triphosgene and base to produce bicycle 2. Treatment of 2 with the appropriate halide and base generates the alkylated bicycle (3). Reaction of 3 with chlorosulfonic acid provided sulfonyl chloride 4. Treatment of 4 with the appropriate aniline provides the target molecule (5).

Scheme 2 above is an exemplary scheme that depicts a representative synthesis of certain compounds described herein. Cyanophenol (10) is reacted lithium aluminumhydride to provide aniline 11. Aniline 11 is treated with triphosgene and base to produce bicycle 12. Treatment of 12 with the appropriate halide and base generates the alkylated bicycle (13). Reaction of 13 with chlorosulfonic acid provided sulfonyl chloride 14. Treatment of 14 with the appropriate aniline provides the target molecule (15).

Scheme 3 above is an exemplary scheme that depicts a representative synthesis of certain compounds described herein. Aniline 20 is reacted with TEBA, chloroacetylchloride and base to produce bicycle 21. Treatment of 21 with the appropriate halide and base generates the alkylated bicycle (22). Reaction of 22 with chlorosulfonic acid provided sulfonyl chloride 23. Treatment of 23 with the appropriate aniline provides the target molecule (24).

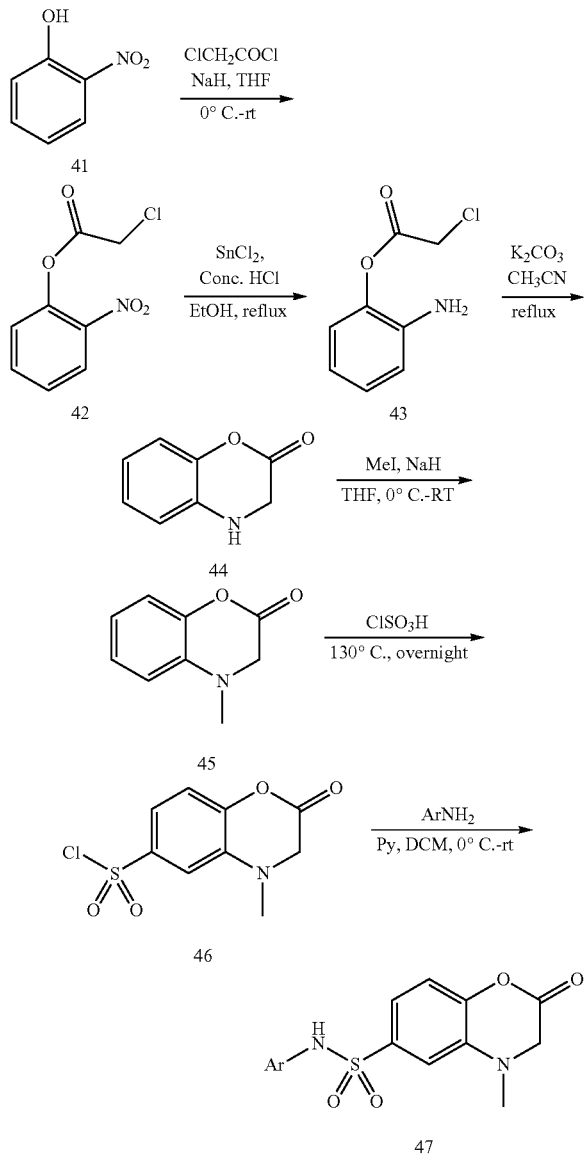

Scheme 4 above is an exemplary scheme that depicts a representative synthesis of certain compounds described herein. Phenol 41 is reacted with chloroacetylchloride and base to produce 42. Treatment of 43 with Tin chloride in acid yielded the desired aniline (43). Treatment of aniline 43 with base produced bicycle 44. Reaction of 44 with the appropriate halide and base generates the alkylated bicycle (45). Reaction of 45 with chlorosulfonic acid provided sulfonyl chloride 46. Treatment of 46 with the appropriate aniline provides the target molecule (47).

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

The compounds of this invention may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Methods of Evaluating Compounds

The compounds described herein can be evaluated for ability to modulate PKM2 (e.g., activate PKM2) by methods known in the art. Exemplary methods include contacting the compound with a cell-based assay which allows assessment of the ability to modulate PKM2 (e.g., activate PKM2). E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate PKM2). The evaluation could also include measuring a change in pyruvate or a determination of an alteration in mitochondrial membrane potential, e.g., as measured by fluorescent potentiometric dyes.

PKM1 and PKM2 for use in the screening method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., E. coli) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 2.

TABLE 2

| Component of Reaction Condition | Amount in Activation Assay |
| --- | --- |
| ADP | 0.1-5.0 mM |
| Phosphoenolpyruvate | 0.1-5.0 mM |
| NADH | 10-1000 µM |
| Lactate dehydrogenase | 0.1-10 units |
| Fructose-1,6-bisphosphate | 0 |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

Candidate activator compounds are chosen if they demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, specific candidate activators of PKM2 can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Methods of Treatment

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, one or more additional compounds to a subject, e.g., a patient, or application or administration of the compound to an isolated tissue or cell, e.g., cell line, from a subject, e.g., a patient, who has a disorder (e.g., a disorder as described herein), or a symptom of a disorder, with the purpose to cure, heal, alleviate, relieve, alter, remedy, ameliorate, improve or affect the disorder or one or more symptoms of the disorder.

As used herein, the term "prevent" is defined as the application or administration of a compound, alone or in combination with, one or more additional compounds to a subject, e.g., a patient, with a predisposition toward a disorder, with the purpose to prevent or delay onset of the disorder or a symptom of the disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Neoplastic Disorders

A compound or composition described herein can be used to treat a neoplastic disorder, in particular a neoplastic disorder characterized by an altered (e.g., decreased) level of PKM2 activity in a patient as compared to the PKM2 level in a patient who is not suffering from a neoplastic disorder (e.g., the same patient at a time prior to suffering from the neoplastic disorder, or a different patient who is not suffering from a neoplastic disorder). A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Without being bound by theory, applicants believe that altered PKM2 levels characterize a subset of all types of cancers, without regard to their nature or origin. Thus, the compounds and methods of this invention are useful to treat any type of cancer that is characterized by altered PKM2 levels.

Exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, a compound described herein is administered together with an additional cancer treatment. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g. a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2 (e.g., activate PKM2). Accordingly, a patient and/or subject can be selected for treatment using a compound described herein by first evaluating the patient and/or subject to determine whether the subject is in need of modulation of PKM2 (e.g., activation of PKM2), and if the subject is determined to be in need of modulation of PKM2, then optionally administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring an increase in PKM2 in a patient, by monitoring the growth, absence of growth, or regression of the cancer (e.g., a tumor). In some embodiments, the patient is evaluated using a radiological assay or evaluation of hemolytic parameters.

EXAMPLES

Example 1

PKM2 Assay

Procedure:
PKM2 stock enzyme solution was diluted in Reaction Buffer

2 μL of compound was added into each well first, and then 180 μL of the Reaction Mix was added.

Reaction mixture with compound (without ADP) was incubated for 30 minutes at 4° C.

Plates were re-equilibrated to room temperature prior to adding 20 μL ADP to initiate the reaction.

Reaction progress was measured as changes in absorbance at 340 nm wavelength at room temperature (25° C.)

Reaction Mix:

PKM2 (50 ng/well), ADP (0.7 mM), PEP (0.15 mM), NADH (180 μM), LDH (2 units) in Reaction Buffer Reaction Buffer:
100 mM KCl, 50 mM Tris pH 7.5, 5 mM MgCl2, 1 mM DTT, 0.03% BSA.

Example 2

Compounds and Their Preparation

Scheme 5:

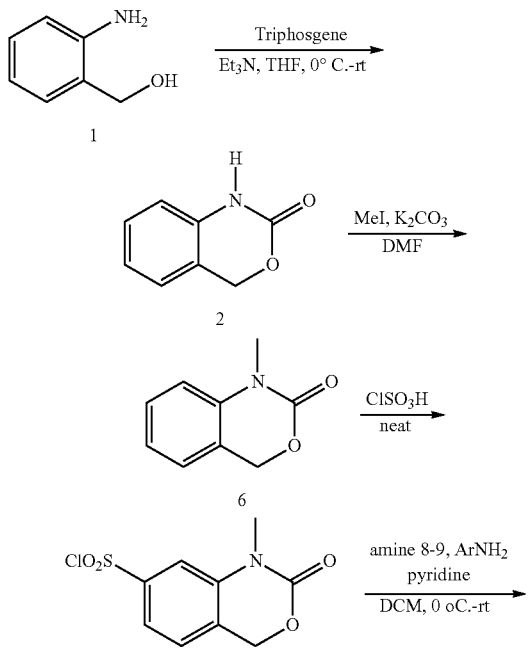

TABLE 5

| Amine | Ar = | Product |
|---|---|---|
| 8 | 3-Cl, 4-F phenyl | 8a |
| 9 | 3-methyl, 4-F phenyl | 9a |

General Procedure for Compound 2:
To a solution of starting material 1 (1.5 gm, 12.10 mmoles) in dry THF, triphosgene (4.3 gm, 14.6 mmoles) in THF was added slowly at 0° C. The resulting mixture was allowed to stir at the same temperature for 10 min. Triethyl amine (6.1 mL, 42.6 mmoles) was then added dropwise at 0° C. and the reaction mixture was allowed to stir at room temperature for another 30 min. After completion of reaction, the reaction mixture was added to crushed ice and extracted with ethyl acetate and water. The organic layer was dried over $Na_2SO_4$ and concentrated under reduced pressure to afford solid product 2 in 66.66% yield (1.81 gm).

General Procedure for Compound 6:
To a solution of compound 2 (3.0 gm, 20.1 mmol) in DMF, potassium carbonate (8.3 gm, 60.4 moles) was added followed by methyl iodide (2 mL, 30.1 mmol) at room temperature. The resulting mixture was stirred for 2 hrs at the same temperature. After completion of the reaction, the mixture was washed with ethyl acetate and water and the organic layer was dried over $Na_2SO_4$ and concentrated under reduced pressure to obtain a residue which turned into a solid compound 6 (2.5 gm, 78.12% yield) on washing with pentane solvent. The obtained product was used for further step directly without purification.

General Procedure for Compound 7:
Compound 6 (3.0 gm, 20.13 mmol) was added to a stirred solution of chlorosulfonic acid (6 mL/gm starting material) at 0° C. and the resulting solution was allowed to stir for 2 hrs at room temperature. After completion of reaction, the mixture was poured into ice cold water and added EtOAc and extracted. The aqueous layer was washed with EtOAc (2×50 ml) and the combined organic layer was washed with brine, dried over $Na_2SO_4$ and concentrated under reduced pressure to obtain a crude residue. The residue was washed with n-hexane to get a solid compound 7 (3.2 gm, 65.30% yield) which was pure enough for the next reaction.

Synthesis of Compound 8a:

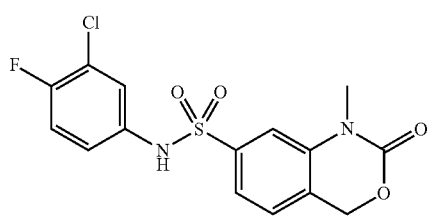 [SMILES: CN1C(=O)OCc2ccc(S(=O)(=O)Nc3ccc(F)c(Cl)c3)cc21]

To a solution of amine 8 (0.13 gm, 0.92 mmol) in DCM, sulfonyl chloride 7 (0.2 gm, 0.76 mmoles) was added followed by addition of pyridine (10 mL/gm starting material) at 0° C. The reaction mixture was allowed to stir at room temperature for 2 hrs. After completion, the reaction mixture was diluted with water and extracted with DCM. The organic layer was washed with 6N HCl, over $Na_2SO_4$ and concentrated under reduced pressure to afford product 8a in 70% yield (0.28 gm).

$^1$H NMR (400 MHz, DMSO-$d_6$) δ 3.21 (s, 3H), 5.31 (s, 1H), 7.04 (br s, 1H), 7.20-7.35 (3H), 7.75-7.68 (m, 2H), 10.45 (s, 1H); MS: 369 (M−1 peak).

Synthesis of Compound 9a:

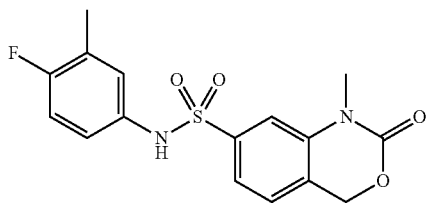 [SMILES: Cc1cc(NS(=O)(=O)c2ccc3c(c2)N(C)C(=O)OC3)ccc1F]

The synthesis of compound 9a was done from compound 7 (0.2 gm, 0.76 mmol) by following the similar procedure carried out to synthesize compound 8a mentioned above by using amine 9 in 74% yield (0.27 gm).

$^1$H NMR (500 MHz, DMSO-$d_6$) δ 2.18 (s, 3H), 3.22 (s, 3H), 5.30 (s, 2H), 6.89 (br s, 1H), 6.99 (d, 2H), 7.21 (d, 1H), 7.72-7.65 (m, 2H), 10.18 (s, 1H); MS: 349 (M−1 peak).

Scheme 6:

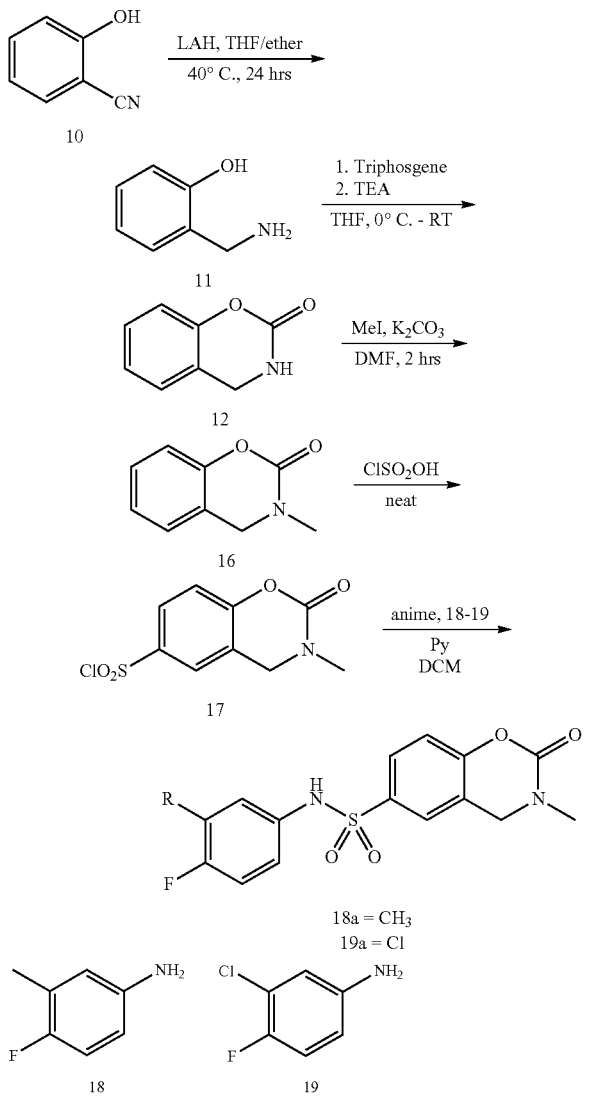

General Procedure for Compound 11:

To a solution of 2-cyano phenol 10 (0.2 gm, 0.075 mmoles) in a dry solvent mixture of THF and ether, LiAlH$_4$ (0.13 gm, 0.018 mmoles) was added at 0° C. portion wise. The resulting mixture was allowed to stir at room temperature for 30 min followed by stirring at 40° C. for 24 hrs. After completion of reaction, the mixture was quenched with saturated NH$_4$Cl solution and extracted with ethyl acetate and water. The organic layer was dried over Na$_2$SO$_4$ and concentrated under reduced pressure to obtain product 11 as a solid in 75% yield. (0.2 gm).

General Procedure for Compound 12:

To a solution of starting material 11 (0.1 gm, 0.081 mmoles) in dry THF, triphosgene (0.29 gm, 0.098 mmoles) was added at 0° C. slowly. The resulting mixture was allowed to stir at the same temperature for 10 min followed by addition of triethyl amine drop wise. The reaction mixture was allowed warm to at room temperature and stirred for 30 min. After completion of reaction, the reaction mixture was added to ice and extracted with ethyl acetate and water. The organic layer was dried over Na$_2$SO$_4$ and concentrated under reduced pressure to obtain product 12 as a solid (0.1 gm, 81.96% yield).

General Procedure for Compound 16:

To a solution of compound 12 (3.0 gm, 20.1 mmol) in DMF, potassium carbonate (8.3 gm, 60.4 moles) was added followed by methyl iodide (2 mL, 30.1 mmol) at room temperature. The resulting mixture was stirred for 2 hrs at the same temperature. After completion of the reaction, the mixture was washed with ethyl acetate and water and the organic layer was dried over Na$_2$SO$_4$ and concentrated under reduced pressure to obtain a residue which turned into a solid compound 16 (2.5 gm, 78.12% yield) on washing with pentane solvent. The obtained product was used for further step directly without purification.

General Procedure for Compound 17:

Compound 16 (3.0 gm, 20.13 mmol) was added to a stirred solution of chlorosulfonic acid (6 mL/gm starting material) at 0° C. and the resulting solution was allowed to stir for 2 hrs at room temperature. After completion of reaction, the mixture was poured into ice cold water and added EtOAc and extracted. The aqueous layer was washed with EtOAc (2×50 ml) and the combined organic layer was washed with brine, dried over Na$_2$SO$_4$ and concentrated under reduced pressure to obtain a crude residue. The residue was washed with n-hexane to get a solid compound 17 (3.2 gm, 65.30% yield) which was pure enough for the next reaction.

Synthesis of Compound 18a:

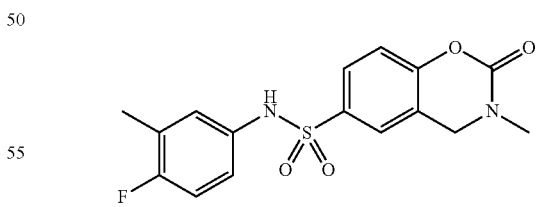

To a solution of amine 18 (0.13 gm, 0.92 mmol) in DCM, sulfonyl chloride 17 (0.2 gm, 0.76 mmoles) was added followed by addition of pyridine (10 mL/gm starting material) at 0° C. The reaction mixture was allowed to stir at room temperature for 2 hrs. After completion, the reaction mixture was diluted with water and extracted with DCM. The organic layer was washed with 6N HCl, over Na$_2$SO$_4$ and concentrated under reduced pressure to afford product 18a in 74% yield (0.2 gm).

¹H NMR (400 MHz, DMSO-d₆) δ 2.16 (s, 3H), 2.98 (s, 3H), 4.53 (s, 2H), 6.88 (br s, 1H), 7.02-6.98 (m, 3H), 7.19 (d, 1H), 7.61 (s, 2H), 10.19 (s, 1H); MS: 349 (M−1 peak).

Synthesis of Compound 19a:

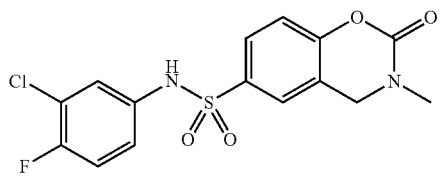 [SMILES: CN1Cc2cc(S(=O)(=O)Nc3ccc(F)c(Cl)c3)ccc2OC1=O]

The synthesis of compound 19a was done from compound 17 (0.2 gm, 0.76 mmol) by following the similar procedure mentioned for compound 19a in scheme 1 in 71% yield (0.2 gm).

¹H NMR (500 MHz, DMSO-d₆) δ 2.98 (s, 3H), 4.55 (s, 2H), 7.06 (br s, 1H), 7.29-7.20 (m, 2H), 7.35 (t, 1H), 7.65 (t, 2H), 10.52 (s, 1H); MS: 369 (M−1 peak).

Scheme 7:

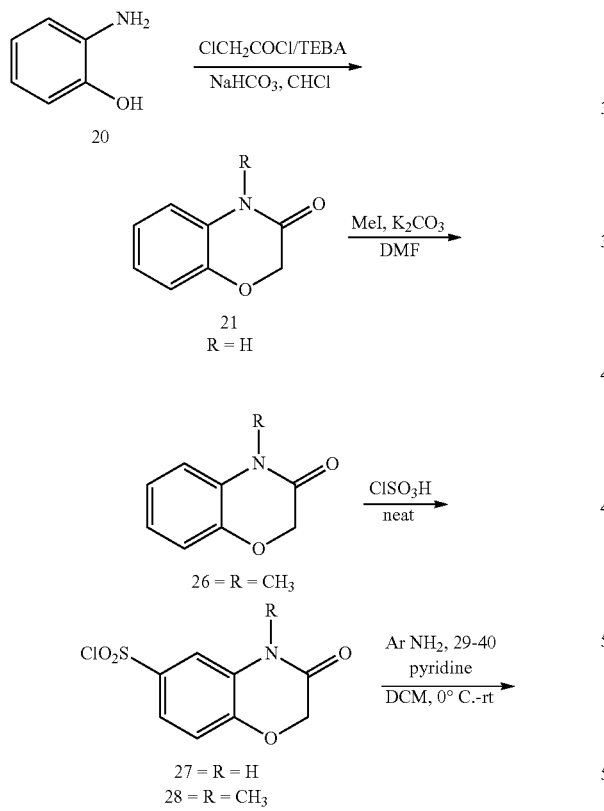

TABLE 6

| Amine | Ar = | R = | Product |
|---|---|---|---|
| 29 | 2,3-dihydro-1,4-benzodioxin-6-yl | CH₃ | 29a |
| 30 | 3,5-dimethylphenyl | CH₃ | 30a |
| 31 | 4-fluorophenyl | CH₃ | 31a |
| 32 | 4-methoxyphenyl | CH₃ | 32a |
| 33 | 4-fluoro-3-methylphenyl | CH₃ | 33a |
| 34 | 3-chloro-4-fluorophenyl | CH₃ | 34a |
| 35 | 3-chlorophenyl | CH₃ | 35a |
| 36 | 1,3-benzodioxol-5-yl | CH₃ | 36a |
| 37 | 3,5-dimethylphenyl | H | 37a |
| 38 | 4-fluorophenyl | H | 38a |

TABLE 6-continued

| Amine | Ar = | R = | Product |
|---|---|---|---|
| 39 | ![structure: benzodioxane] | H | 39a |
| 40 | ![structure: 4-methoxyphenyl]—OMe | H | 40a |

General Procedure for Compound 21:

To a solution of 2-amino phenol 20 (3.0 gm, 27.5 mmoles) in chloroform, TEBA (3.1 gm, 13.7 mmol) and NaHCO$_3$ was added at 0° C. Then a solution of chloro acetyl chloride (4.6 gm, 41.2 m moles) in chloroform was added over 20 minutes at the same temperature and the resulting mixture was allowed to stir at 60° C. for 16 hrs. After completion of the reaction, solvent was evaporated and washed with DCM and water. The organic layer was dried over Na$_2$SO$_4$ and concentrated under vacuum. The resulting solution was washed with pentane and ether as a co-solvent to get compound 21 (3.2 gm, 78.04% yield) as solid which was pure enough to use directly for further reaction.

General Procedure for Compound 26:

To a solution of compound 21 (3.0 gm, 20.1 mmol) in DMF, potassium carbonate (8.3 gm, 60.4 moles) was added followed by methyl iodide (2 mL, 30.1 mmol) at room temperature. The resulting mixture was stirred for 2 hrs at the same temperature. After completion of the reaction, the mixture was washed with ethyl acetate and water and the organic layer was dried over Na$_2$SO$_4$ and concentrated under reduced pressure to obtain a residue which turned into a solid compound 26 (2.5 gm, 78.12% yield) on washing with pentane solvent. The obtained product was used for further step directly without purification.

General Procedure for Compound 27:

Compound 26 (3.0 gm, 20.13 mmol) was added to a stirred solution of chlorosulfonic acid (6 mL/gm starting material) at 0° C. and the resulting solution was allowed to stir for 2 hrs at room temperature. After completion of reaction, the mixture was poured into ice cold water and added EtOAc and extracted. The aqueous layer was washed with EtOAc (2×50 ml) and the combined organic layer was washed with brine, dried over Na$_2$SO$_4$ and concentrated under reduced pressure to obtain a crude residue. The residue was washed with n-hexane to get a solid compound 27 (3.2 gm, 65.30% yield) which was pure enough for the next reaction.

General Procedure for Compound 28:

Starting material 26 (2.0 gm, 12.2 mmol) was added to a stirred solution of chlorosulfonic acid (6 mL/gm starting material) at 0° C. and the resulting solution was allowed to stir for 2 hrs at room temperature. After completion of reaction, mixture was poured into ice cold water and added ethyl acetate and extracted. The aqueous layer was washed with EtOAc (2×50 ml) and the combined organic layers was washed with brine and dried over Na$_2$SO$_4$ and concentrated under reduced pressure to obtain residue. The residue was washed with n-hexane to get solid compound 28 (2.5 gm, 78.1% yield). Thus obtained product was used for further step directly.

Synthesis of Compound 29a:

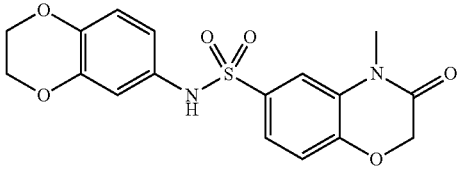 [SMILES: CN1C(=O)COc2ccc(S(=O)(=O)Nc3ccc4c(c3)OCCO4)cc21]

To a solution of amine 29 (0.07 gm, 0.463 mmol) in DCM, sulfonyl chloride 28 (0.14 gm, 0.35 mmoles) was added followed by pyridine (10 mL/gm starting material) at 0° C. and the reaction mixture was allowed to stir at room temperature for 2 hrs. After completion, the reaction mixture was diluted with water and extracted with DCM. The organic layer was washed with 6N HCl and dried over Na$_2$SO$_4$ and concentrated under reduced pressure to obtain product 29a (0.10 gm, 58.8% yield).

$^1$H NMR (500 MHz, DMSO-d$_6$) δ 3.21 (s, 3H), 4.19 (s, 4H), 4.78 (s, 2H), 6.58 (d, 1H), 6.6 (s, 1H), 6.71 (d, 1H), 7.15 (d, 1H), 7.34 (d, 1H), 7.29 (s, 1H), 9.83 (s, 1H). MS: 375 (M−1 peak).

Synthesis of Compound 30a:

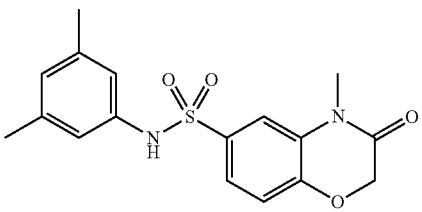 [SMILES: Cc1cc(C)cc(NS(=O)(=O)c2ccc3c(c2)N(C)C(=O)CO3)c1]

The synthesis of compound 30a was done by following the similar procedure as mentioned for compound 29a by using amine 30 to afford product 30a in 60% yield (0.12 gm) from compound 28 (0.18 gm, 0.69 mmoles).

$^1$H NMR (500 MHz, DMSO-d$_6$) δ 2.18 (s, 6H), 3.21 (s, 3H), 4.78 (s, 2H), 6.65 (s, 1H), 6.78 (s, 2H), 7.15 (d, 1H), 7.39 (d, 1H), 7.41 (s, 1H), 10.08 (s, 1H); MS: 345 (M−1 peak).

Synthesis of Compound 31a:

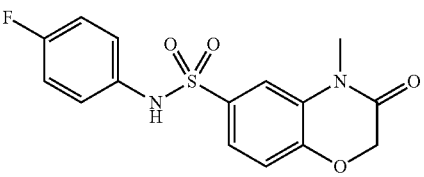 [SMILES: CN1C(=O)COc2ccc(S(=O)(=O)Nc3ccc(F)cc3)cc21]

The synthesis of compound 31a was done by following the similar procedure as mentioned for compound 29a by using amine 31 to afford product 31a in 61.1% yield (0.13 gm) from compound 28 (0.2 gm, 0.76 mmol).

$^1$H NMR (500 MHz, DMSO-d$_6$) δ 3.21 (s, 3H), 4.78 (s, 2H), 7.15-7.04 (m, 5H), 7.35 (d, 1H), 7.39 (s, 1H), 10.10 (s, 1H); MS: 335 (M−1 peak).

Synthesis of Compound 32a:

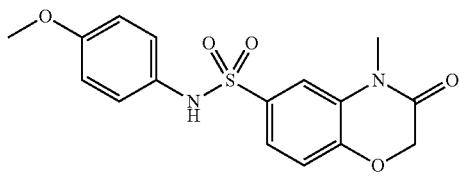 [SMILES: COc1ccc(NS(=O)(=O)c2ccc3c(c2)N(C)C(=O)CO3)cc1]

The synthesis of compound 32a was done by following the similar procedure as mentioned for compound 29a by using amine 32 to afford product 32a in 63.15% yield (0.12 gm) from compound 28 (0.18 gm, 0.68 mmol).

$^1$H NMR (500 MHz, DMSO-d$_6$) δ 3.20 (s, 3H), 3.66 (s, 3H), 4.78 (s, 2H), 6.81 (d, 2H), 7.01 (d, 2H), 7.09 (d, 1H), 7.29 (dd, 1H), 7.35 (d, 1H), 9.81 (s, 1H); MS: 349 (M+1 peak).

Synthesis of Compound 33a:

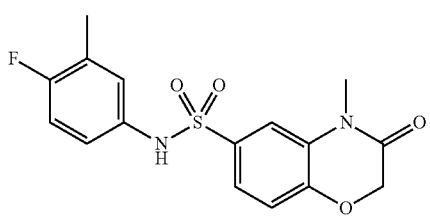 [SMILES: Cc1cc(NS(=O)(=O)c2ccc3c(c2)N(C)C(=O)CO3)ccc1F]

The synthesis of compound 33a was done by following the similar procedure as mentioned for compound 29a by using amine 33 to afford product 33a in 53% yield (0.15 gm) from compound 28 (0.25 gm, 0.96 mmol).

$^1$H NMR (400 MHz, DMSO-d$_6$) δ 2.16 (s, 3H), 3.21 (s, 3H), 4.75 (s, 3H), 6.91 (br s, 7.14-6.90 (m, 4H), 7.40-7.32 (m, 2H), 10.15 (s, 1H).

Synthesis of Compound 34a:

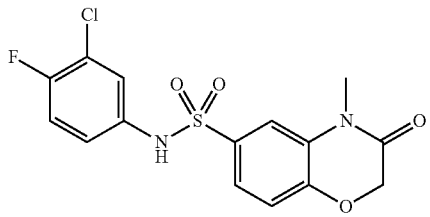 [SMILES: CN1C(=O)COc2ccc(S(=O)(=O)Nc3ccc(F)c(Cl)c3)cc21]

The synthesis of compound 34a was done by following the similar procedure as mentioned for compound 29a by using amine 34 to afford product 34a in 48% yield (0.12 gm) from compound 28 (0.21 gm, 0.82 mmol).

$^1$H NMR (400 MHz, DMSO-d$_6$) δ 3.21 (s, 3H), 4.78 (s, 2H), 7.18-7.03 (m, 2H), 7.27-7.22 (m, 4H), 10.42 (s, 1H).

Synthesis of Compound 35a:

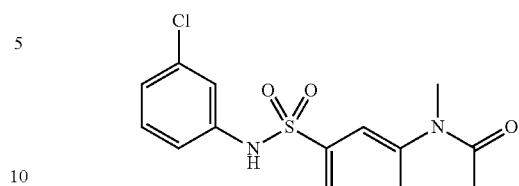

The synthesis of compound 35a was done by following the similar procedure as mentioned for compound 29a by using amine 35 to afford product 35a in 48.14% yield (0.13 gm) from compound 28 (0.24 gm, 0.94 mmol).

$^1$H NMR (400 MHz, DMSO-d$_6$) δ 3.22 (s, 3H), 4.78 (s, 2H), 7.21-7.02 (m, 4H), 7.29 (t, 1H), 7.41 (d, 2H), 10.55 (s, 1H).

Synthesis of Compound 36a:

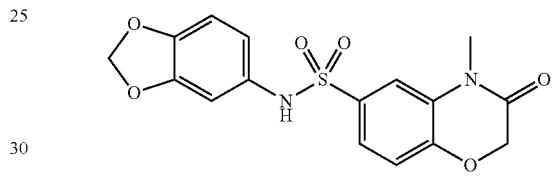

The synthesis of compound 36a was done by following the similar procedure as mentioned for compound 29a by using amine 36 to afford product 36a in 63% yield (0.10 gm) from compound 28 (0.15 gm, 0.56 mmol).

$^1$H NMR (400 MHz, DMSO-d$_6$) δ 3.21 (s, 3H), 4.76 (s, 2H), 5.98 (s, 2H), 6.51 (d, 1H), 6.71 (s, 1H), 6.79 (d, 1H), 7.11 (d, 1H), 7.34 (d, 1H), 7.39 (s, 1H), 9.93 (s, 1H); MS: 361 (M−1 peak).

Synthesis of Compound 37a:

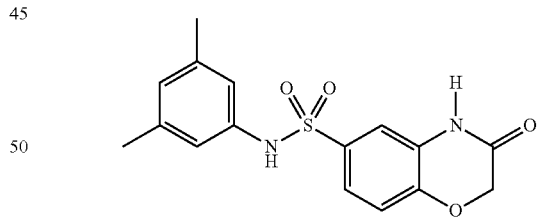

To a solution of amine 37 (0.07 gm, 0.57 mmoles) in DCM, sulfonyl chloride 27 (0.17 gm, 0.69 mmoles) was added followed by pyridine (10 mL/gm starting material) at 0° C. and the reaction mixture was allowed to stir at room temperature for 2 hrs. After completion, the reaction mixture was diluted with water and extracted with DCM. The organic layer was washed with 6N HCl and dried over Na$_2$SO$_4$ and concentrated under reduced pressure to afford product 37a (0.12 gm, 63.15% yield).

$^1$H NMR (500 MHz, DMSO-d$_6$) δ 2.18 (s, 6H), 4.63 (s, 2H), 6.64 (s, 1H), 6.74 (s, 2H), 7.04 (d, 1H), 7.31 (d, 2H), 10.05 (s, 1H), 10.97 (s, 1H); MS: 333 (M+1 peak).

Synthesis of Compound 38a:

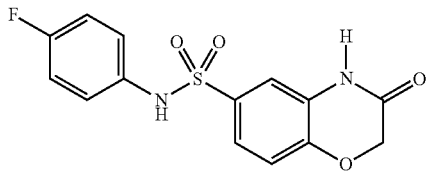 [SMILES: O=C1COc2ccc(S(=O)(=O)Nc3ccc(F)cc3)cc2N1]

The synthesis of compound 38a was done by following the similar procedure as mentioned for compound 37a by using amine 38 to afford product 38a in 65% yield (0.13 gm) from compound 27 (0.19 gm, 0.756 mmol).

$^1$H NMR (500 MHz, DMSO-$d_6$) δ 4.65 (s, 2H), 7.13-7.03 (m, 5H), 7.25 (s, 2H), 10.09 (s, 1H), 10.97 (s, 1H); MS: 320 (M−2 peak).

Synthesis of Compound 39a:

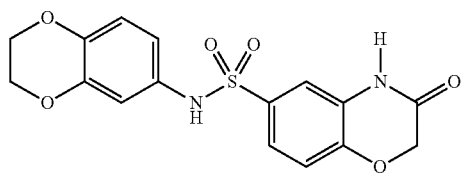 [SMILES: O=C1COc2ccc(S(=O)(=O)Nc3ccc4c(c3)OCCO4)cc2N1]

The synthesis of compound 39a was done by following the similar procedure as mentioned for compound 37a by using amine 39 to afford product 39a in 62% yield (0.10 gm) from compound 27 (0.14 gm, 0.56 mmol).

$^1$H NMR (500 MHz, DMSO-$d_6$) δ 4.18 (s, 4H), 4.66 (s, 2H), 6.53 (d, 1H), 6.60 (s, 1H), 6.74 (s, 1H), 7.06 (d, 1H), 7.2 (d, 2H), 9.92 (s, 1H), 10.93 (s, 1H); MS: 361 (M−1 peak).

Synthesis of Compound 40a:

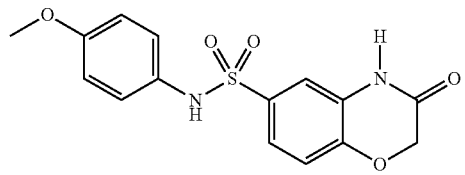

The synthesis of compound 40a was done by following the similar procedure as mentioned for compound 37a by using amine 40 to afford product 40a in 63.15% yield (0.12 gm) from compound 27 (0.17 gm, 0.68 mmol).

$^1$H NMR (500 MHz, DMSO-$d_6$) δ 3.65 (s, 3H), 4.64 (s, 2H), 6.8 (d, 2H), 6.97 (d, 2H), 7.03 (d, 1H), 7.25-7.20 (m, 2H), 9.93 (s, 1H), 10.93 (s, 1H); MS: 332 (M−2 peak).

Scheme 2:

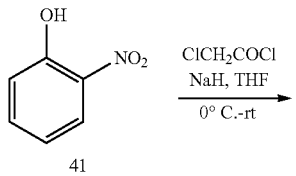

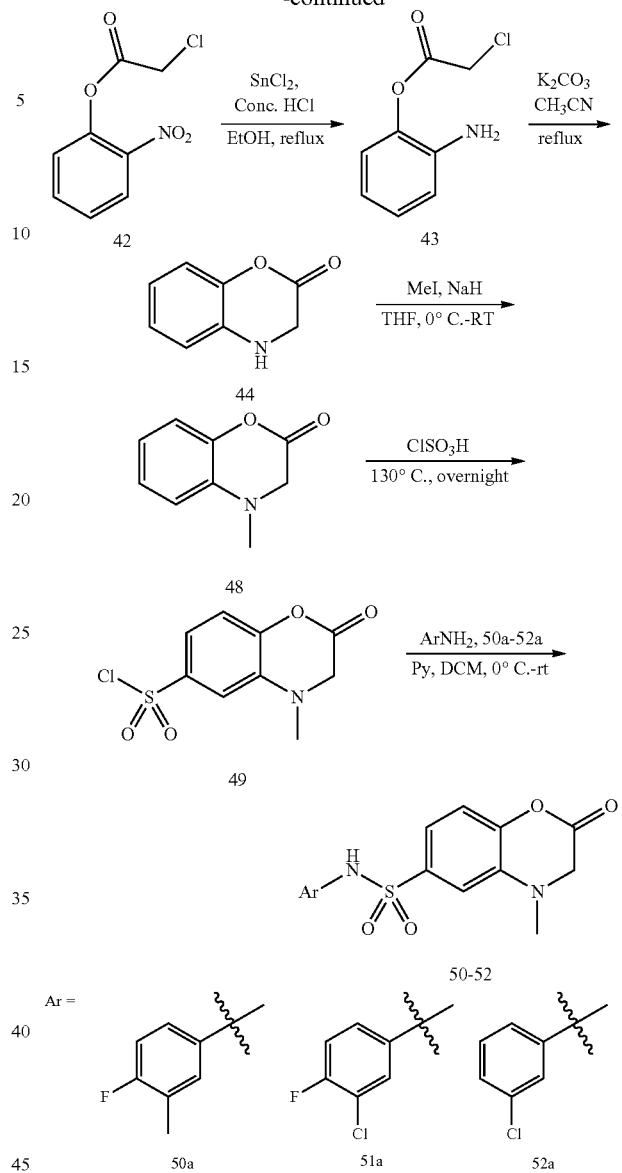

General Procedure for Compound 42:

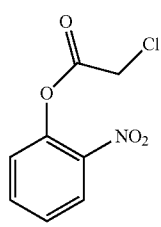

To a stirred suspension of activated NaH (0.24 gm, 10.00 mmol) in THF, 2-nitrophenol (41) (1.0 gm, 7.1 mmol) was added at 0° C. under $N_2$ atmosphere and stirred for 15 min followed by addition of chloroacetylchloride (1.2 gm, 10.0 mmoles) at the same temperature and allowed to stir at room temperature for 1 hr. After completion of reaction, the mixture was poured into ice and extracted with ethyl acetate. The organic layer dried over Na$_2$SO$_4$ and concentrated under reduced pressure to obtain product 42 in 71% yield (1.1 gm).

General Procedure for Compound 43:

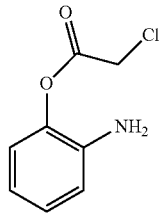 [SMILES: O=C(CCl)Oc1ccccc1[N+](=O)[O-]]

To a stirred solution of nitro compound 42 (6.3 gm, 29.3 mmol) in ethanol was added conc. HCl (5 mL) followed by addition of 5 nCl$_2$ (33.0 gm, 146.5 mmol) and refluxed for 2 hrs under nitrogen atmosphere. After completion of reaction, ethanol was removed under reduced pressure and the obtained mass was dissolved in water and neutralized with saturated sodium bicarbonate solution and extracted with ethyl acetate. The organic layer dried over Na$_2$SO$_4$ and concentrated to obtain product 43 (1.3 gm; 24.07% yield).

General Procedure for Compound 44:

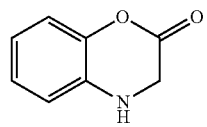 [SMILES: O=C1CNc2ccccc2O1]

To the stirred solution of aniline 43 (1.0 gm, 5.4 mmoles) in acrylonitrile K$_2$CO$_3$ (3.7 gm, 27.0 mmol) was added at room temperature under N$_2$ atmosphere and the resulting mixture was allowed to reflux overnight. After completion of reaction, the mixture was diluted with water and extracted with ethyl acetate. The organic layer dried over Na$_2$SO$_4$ and concentrated under reduced pressure to obtain product (0.80 gm, 100% yield).

General Procedure for Compound 48:

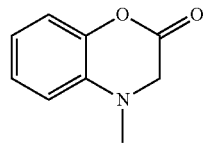

To a solution of NaH (0.072 gms, 3.0 mmol) in THF, amino lactone 44 (0.31 gm, 2.0 mmol) was added at 0° C. slowly and stirred for 30 min followed by addition of MeI (0.21 ml, 3.0 moles) at the same temperature and the resulting mixture was stirred for 1 hr. After completion of reaction, the mixture was poured in ice water and extracted with ethylacetate, dried over Na$_2$SO$_4$, and concentrated under reduced pressure to obtain the product (0.9 gm, 90.0% yield).

General Procedure for Compound 49:

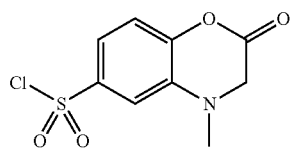 [SMILES: CN1CC(=O)Oc2ccc(S(=O)(=O)Cl)cc21]

Chlorosulfonic acid (10 ml/gm starting material) was added slowly to amino lactone 48 (1.1 gm, 6.0 moles) in de-aerated RB flask at 0° C. and resulting mixture was heated to 160° C. for overnight. After completion of reaction, the mixture was added to ice and extracted with ethylacetate and the organic layer dried over Na$_2$SO$_4$, and concentrated under reduced pressure to obtain product. (1.0 gm, 58.8% yield).

Synthesis of Compound 50:

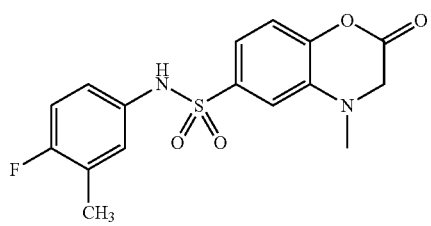 [SMILES: Cc1cc(NS(=O)(=O)c2ccc3c(c2)N(C)CC(=O)O3)ccc1F]

To a solution of sulfonyl chloride 49 (0.2 gm, 0.76 moles) and pyridine (0.15 gm, 1.91 mmol) in DCM, amine 50a (0.14 gm, 1.07 mmoles) was added at 0° C. and the resulting mixture was allowed to stir at room temperature for 3 hrs. After completion of reaction, DCM was removed under reduced pressure and the residue was extracted with ethyl acetate and water. The organic layer was washed with brine and dried over Na$_2$SO$_4$. The organic layer was concentrated to afford product 50 in 74% yield (0.1 gm).

$^1$H NMR (500 MHz, DMSO-d$_6$) δ 2.21 (s, 3H), 3.24 (s, 3H), 4.70 (s, 2H), 6.37 (s, 1H), 6.96-6.80 (m, 3H), 7.00 (d, 1H), 7.39 (d, 1H); MS: 349 (M−1 peak).

Synthesis of Compound 51:

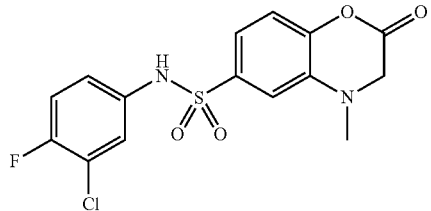 [SMILES: CN1CC(=O)Oc2ccc(S(=O)(=O)Nc3ccc(F)c(Cl)c3)cc21]

The synthesis of compound 51 was done by following the same procedure similar to compound 50 using the compound 51a instead of 50a to get the compound 51 (0.13 gm, 92.19% yield) from compound 49 (0.1 gm, 0.38 mmoles).

$^1$H NMR (500 MHz, DMSO-d$_6$) δ 3.30 (s, 3H), 4.70 (s, 2H), 6.55 (s, 1H), 6.99-6.92 (m, 1H), 7.08-7.01 (m, 3H), 7.20 (br s, 1H), 7.35 (s, 1H), 7.40 (d, 1H); MS: 369 (M−1 peak).

Synthesis of Compound 52:

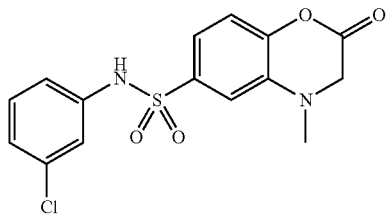 [SMILES: CN1CC(=O)Oc2ccc(S(=O)(=O)Nc3cccc(Cl)c3)cc21]

The synthesis of compound 52 was done from compound 49 (0.2 gm, 0.76 mmol) by following the same procedure similar to compound 50 using the amine 52a instead of 50a to get the compound 52 (0.2 gm, 74.34% yield).

$^1$H NMR (500 MHz, DMSO-$d_6$) δ 3.21 (s, 3H), 4.75 (s, 2H), 7.18-7.02 (m, 3H), 7.28 (t, 1H), 7.41 (d, 2H); MS: 351 (M+1 peak).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of formula (I),

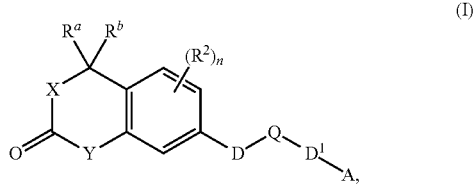

or a pharmaceutically acceptable salt thereof, wherein:
X and Y are each independently selected from O and N(-L-$R^1$), wherein X is O and Y is N(-L-$R^1$) or X is N(-L-$R^1$) and Y is O;
Q is C(O), $SO_2$, or —$(CH_2)_h$—;
each L is independently selected from a bond, —C(O)—, —$(CR^aR^b)_m$—, —C(O)N($R^c$)— or —C(O)O—;
D and $D^1$ are each independently selected from a bond, O and N($R^c$), provided that D and $D^1$ are not both a bond;
A is aryl or heteroaryl, each of which is substituted with 0-3 occurrences of $R^d$; and D-Q-$D^1$-A is not $OCH_2$-phenyl;
each $R^1$ is independently selected from hydrogen, $C_{1-4}$ alkyl, halo $C_{1-4}$alkyl, alkyl-O-alkylene, $C_{3-10}$ cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$;
each $R^a$ and each $R^b$ are independently selected from hydrogen, $C_{1-4}$ alkyl, or $R^a$ and $R^b$ bound to the same carbon atom are taken together with the carbon atom to form a cycloalkyl;
each $R^c$ is independently selected from hydrogen and $C_{1-4}$ alkyl;
each $R^d$ is independently selected from halo, halo $C_{1-4}$ alkyl, $C_{1-4}$ alkyl, nitro, cyano, —OH and —O($C_{1-4}$ alkyl), or two $R^d$, attached to the same or adjacent carbon atoms, taken together with the atom(s) to which they are attached form an optionally substituted heterocyclyl;
each $R^f$ is independently selected from halo, halo $C_{1-4}$alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;
each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;
each $R^2$ is independently selected from halo, halo $C_{1-4}$ alkyl, $C_{1-4}$ alkyl, $C_{1-4}$ alkoxy and hydroxyl;
h is 1, 2 or 3;
each m is independently 1, 2 or 3; and
each n is independently 0, 1, 2 or 3;
provided that the compound is not 2-chloro-N-(1,4-dihydro-2-oxo-2H-3,1-benzoxazin-7-yl)-5-[[(1-methylethyl)amino]sulfonyl]-benzamide; or
4-[2-oxo-7-(phenylmethoxy)-2H-1,3-benzoxazin-3(4H)-yl], Benzoic methyl ester.

2. The compound of claim 1, wherein the compound is a compound of formula (Ia):

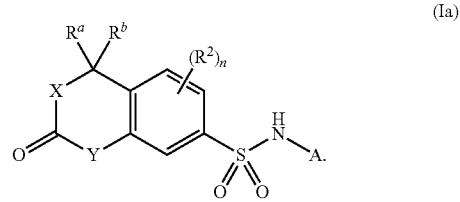

3. The compound of claim 1, selected from:

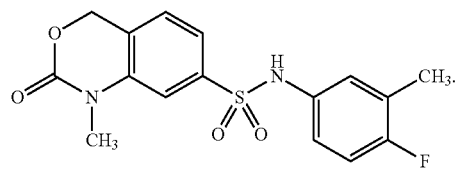 [SMILES: Cc1cc(NS(=O)(=O)c2ccc3c(c2)N(C)C(=O)OC3)ccc1F]

4. A compound of formula (II):

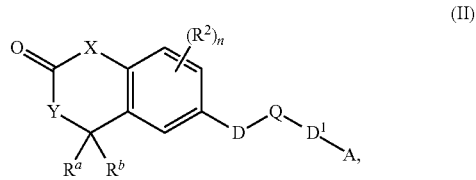

or a pharmaceutically acceptable salt thereof, wherein:
X and Y are each independently selected from O and N-L-$R^1$, wherein X is O and Y is N(-L-$R^1$) or X is N(-L-$R^1$) and Y is O;
Q is C(O), $SO_2$, or —$(CH_2)_h$—;
each L is independently selected from a bond, —C(O)—, —$(CR^aR^b)_m$—, —C(O)N$R^c$— or —C(O)O—;
D and $D^1$ are each independently selected from a bond, O and N$R^c$, provided that D and $D^1$ are not both a bond;

A is aryl or heteroaryl, each of which is substituted with 0-3 occurrences of $R^d$;

each $R^1$ is independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$;

each $R^a$ and each $R^b$ are independently selected from hydrogen, $C_{1-4}$ alkyl, or $R^a$ and $R^b$ bound to the same carbon atom are taken together with the carbon atom to form a cycloalkyl;

each $R^c$ is independently selected from hydrogen and $C_{1-4}$ alkyl;

each $R^d$ is independently selected from halo, halo $C_{1-4}$ alkyl, $C_{1-4}$ alkyl, nitro, cyano, —OH and —O($C_{1-4}$ alkyl), or two $R^d$, attached to the same or adjacent carbon atoms, taken together with the atoms to which they are attached form an optionally substituted heterocyclyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl;

h is 1, 2 or 3;

each m is independently 1, 2 or 3; and each n is independently 0, 1, 2 or 3; provided that 1) D-Q-D$^1$-A is not i) O-benzyl, ii) NHSO$_2$-2-thiophenyl, iii) NHC(O)-optionally substituted phenyl, or iv) NHSO$_2$-optionally substituted phenyl; and 2) the compound is not:
   i) N-[2-[[[(1S)-2-cyclohexyl-1-methylethyl]amino]methyl]phenyl]-1,4-dihydro-2-oxo-2H-3,1-Benzoxazine-6-sulfonamide; or
   ii) N-[2-[[[(1S)-2-cyclopentyl-1-methylethyl]amino]methyl]phenyl]-1,4-dihydro-2-oxo-2H-3,1-Benzoxazine-6-sulfonamide.

5. The compound of claim 4, wherein the compound is a compound of formula (IIa):

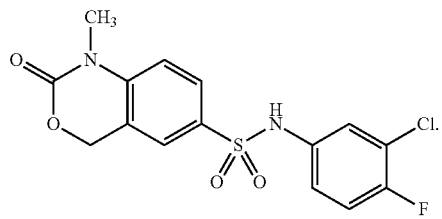

(IIa)

6. The compound of claim 4, selected from:

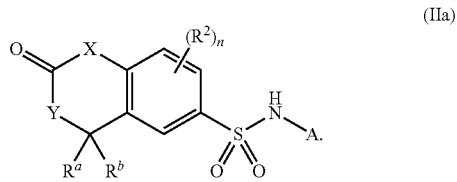

7. A compound of formula (IIIa):

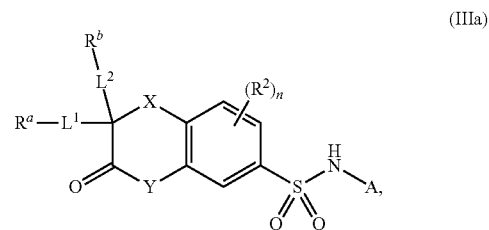

(IIIa)

or a pharmaceutically acceptable salt thereof, wherein:

X is O and Y is N(-L-R$^1$), or X is N(-L-R$^1$) and Y is O;

$L^1$ and $L^2$ are each independently selected from a bond, —O—, C(O)—, —C(O)O—, —OC(O)—, —C(O)NR$^c$—, —NR$^c$C(O)—, —S—, —SO— and —SO$_2$—;

A is aryl or heteroaryl, each of which is substituted with 0-3 occurrences of $R^f$;

each $R^1$ is independently selected from hydrogen or $C_{1-4}$ alkyl, wherein each $C_{1-4}$ alkyl is substituted with 0-3 occurrences of $R^f$;

$R^a$ and $R^b$ are each independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocyclylalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$; or one of $R^a$ or $R^b$ is taken together with $R^1$ and the atoms to which they are respectively attached to form an optionally substituted five-membered heterocylyl;

each $R^c$ is independently selected from hydrogen and $C_{1-4}$ alkyl;

each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;

each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;

each $R^2$ is independently selected from halo, halo $C_{1-4}$ alkyl, $C_{1-4}$ alkyl, $C_{1-4}$ alkoxy and hydroxyl; and n is 0, 1, 2 or 3; provided that the compound is not:
   i) N-(3-fluoro-2-methylphenyl)-3,4-dihydro-4-methyl-3-oxo-2H-1,4-benzoxazine-6-sulfonamide; or ii) methyl 4,5-dimethoxy-2-(4-methyl-3-oxo-3,4-dihydro-2H-benzo[b][1,4]oxazine-6-sulfonamido)-phenethylcarbamate.

8. The compound of claim 7, selected from:

9. A compound of formula (IVa):

(IVa)

or a pharmaceutically acceptable salt thereof, wherein:
X is O and Y is N—$R^1$;
$L^1$ and $L^2$ are each independently selected from a bond, —O—, C(O)—, —C(O)O—, —OC(O)—, —C(O)NR$^c$—, —NR$^c$C(O)—, —S—, —SO— and —SO$_2$—;
A is aryl or heteroaryl, each of which is substituted with 0-3 occurrences of $R^d$;
each $R^1$ is independently selected from hydrogen or $C_{1-4}$ alkyl; wherein each $C_{1-4}$ alkyl is substituted with 0-3 occurrences of $R^f$;
$R^a$ and $R^b$ are each independently selected from hydrogen, $C_{1-4}$ alkyl, halo$C_{1-4}$ alkyl, alkyl-O-alkylene, cycloalkyl, aryl, aralkyl, heteroaryl, heteroaralkyl, heterocyclyl and heterocycloalkyl; wherein each alkyl-O-alkylene, cycloalkyl, aryl, aralkyl, heteroaryl, heteroaralkyl, heterocyclyl and heterocyclylalkyl is substituted with 0-3 occurrences of $R^f$ and each alkyl and haloalkyl is substituted with 0-3 occurrences of $R^g$; or
one of $R^a$ or $R^b$ is taken together with a Y—$R^1$ or X—$R^1$ and the atoms to which they are respectively attached to form an optionally substituted five-membered heterocyclyl;
each $R^c$ is independently selected from hydrogen and $C_{1-4}$ alkyl;
each $R^d$ is independently selected from halo, halo $C_{1-4}$ alkyl, $C_{1-4}$ alkyl, nitro, —NR$^c$R$^c$, —NHCH(NR$^c$R$^c$)NR$^c$ R$^c$, —NHC(=NR$^c$R$^c$)NR$^c$R$^c$, —C(O)NR$^c$R$^c$, cyano, —SR$^c$ and —OR', or two $R^d$, attached to the same or adjacent carbon atoms, taken together with the atoms to which they are attached form an optionally substituted heterocyclyl;
each $R^f$ is independently selected from halo, halo $C_{1-4}$ alkyl, $C_{1-4}$ alkyl, nitro, cyano, —OH and —O($C_{1-4}$ alkyl), or two $R^f$, attached to the same or adjacent carbon atoms, taken together with the atoms to which they are attached form an optionally substituted heterocyclyl;
each $R^g$ is independently selected from nitro, cyano, —OH, —O($C_{1-4}$ alkyl) or two $R^g$, attached to the same or adjacent carbon atoms, taken together with the atoms to which they are attached form an optionally substituted heterocyclyl;
each $R^2$ is independently selected from halo, halo $C_{1-4}$ alkyl, $C_{1-4}$ alkyl, $C_{1-4}$ alkoxy and hydroxyl;
h is 1, 2 or 3; and
n is 0, 1, 2 or 3.

10. The compound of claim 9, selected from:

11. A pharmaceutical composition comprising a compound of claim 1 or a pharmaceutically acceptable salt thereof and a pharmaceutically acceptable carrier.

12. The compound of claim 1, selected from:

13. The compound of claim 4, selected from:

14. The compound of claim 4, selected from:

15. The compound of claim 4, selected from:

16. The compound of claim 4, selected from:

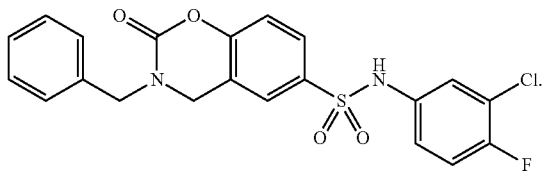 [SMILES: O=C1Oc2ccc(S(=O)(=O)Nc3ccc(F)c(Cl)c3)cc2CN1Cc1ccccc1]

17. The compound of claim 7, selected from:

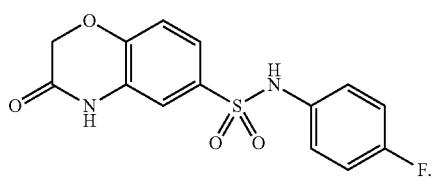 [SMILES: O=C1COc2ccc(S(=O)(=O)Nc3ccc(F)cc3)cc2N1]

18. The compound of claim 7, selected from:

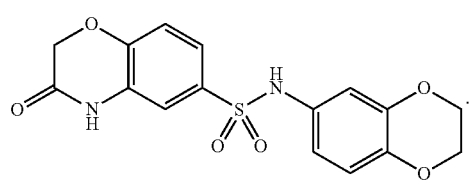 [SMILES: O=C1COc2ccc(S(=O)(=O)Nc3ccc4c(c3)OCCO4)cc2N1]

19. The compound of claim 7, selected from:

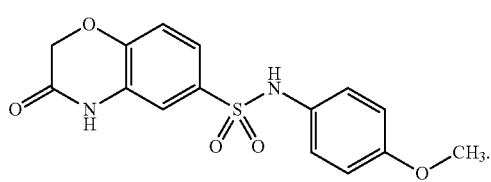 [SMILES: COc1ccc(NS(=O)(=O)c2ccc3c(c2)NC(=O)CO3)cc1]

20. The compound of claim 7, selected from:

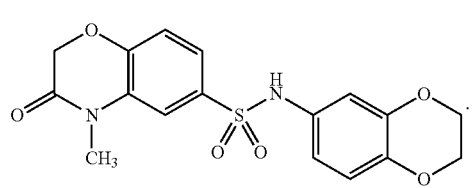 [SMILES: CN1C(=O)COc2ccc(S(=O)(=O)Nc3ccc4c(c3)OCCO4)cc21]

21. The compound of claim 7, selected from:

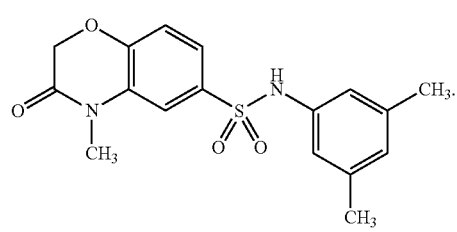 [SMILES: Cc1cc(C)cc(NS(=O)(=O)c2ccc3c(c2)N(C)C(=O)CO3)c1]

22. The compound of claim 7, selected from:

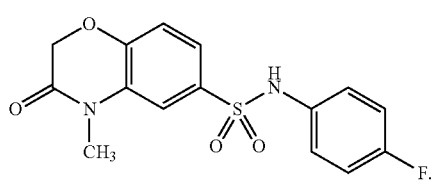 [SMILES: CN1C(=O)COc2ccc(S(=O)(=O)Nc3ccc(F)cc3)cc21]

23. The compound of claim 7, selected from:

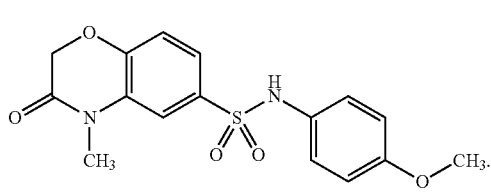 [SMILES: COc1ccc(NS(=O)(=O)c2ccc3c(c2)N(C)C(=O)CO3)cc1]

24. The compound of claim 7, selected from:

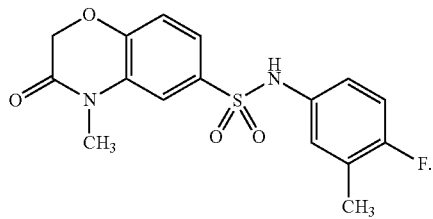 [SMILES: Cc1cc(NS(=O)(=O)c2ccc3c(c2)N(C)C(=O)CO3)ccc1F]

25. The compound of claim 7, selected from:

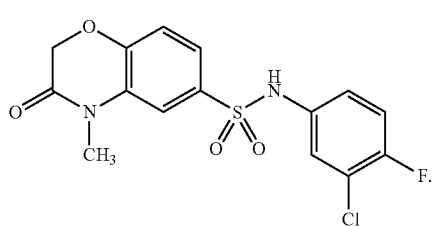 [SMILES: CN1C(=O)COc2ccc(S(=O)(=O)Nc3ccc(F)c(Cl)c3)cc21]

26. The compound of claim 7, selected from:

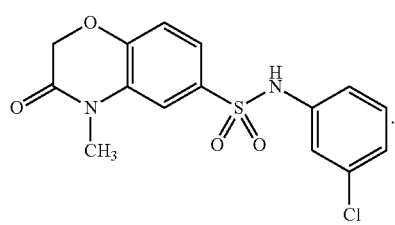 [SMILES: CN1C(=O)COc2ccc(S(=O)(=O)Nc3cccc(Cl)c3)cc21]

27. The compound of claim 7, selected from:
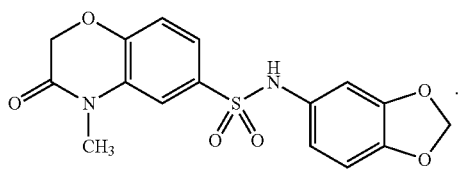 [SMILES: CN1C(=O)COc2ccc(S(=O)(=O)Nc3ccc4c(c3)OCO4)cc21]
28. The compound of claim 9, selected from:
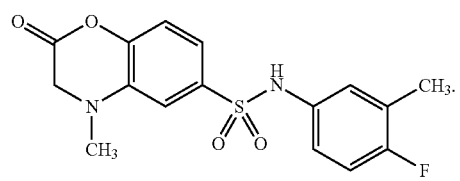 [SMILES: Cc1cc(NS(=O)(=O)c2ccc3c(c2)N(C)CC(=O)O3)ccc1F]
29. The compound of claim 9, selected from:
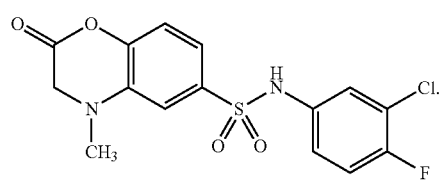 [SMILES: CN1CC(=O)Oc2ccc(S(=O)(=O)Nc3ccc(F)c(Cl)c3)cc21]
* * * * *